US012296105B2

(12) United States Patent
Higashiyama

(10) Patent No.: US 12,296,105 B2
(45) Date of Patent: May 13, 2025

(54) HUMIDIFICATION APPARATUS AND HUMIDIFICATION AND BLOWING APPARATUS FOR RESPIRATORY ORGANS INCLUDING THE SAME

(71) Applicant: Murata Manufacturing Co., Ltd., Nagaokakyo (JP)

(72) Inventor: Yuzo Higashiyama, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 854 days.

(21) Appl. No.: 17/183,446

(22) Filed: Feb. 24, 2021

(65) Prior Publication Data
US 2021/0178108 A1   Jun. 17, 2021

Related U.S. Application Data

(63) Continuation of application No. PCT/JP2019/031966, filed on Aug. 14, 2019.

(30) Foreign Application Priority Data

Aug. 29, 2018   (JP) .................................. 2018-160393

(51) Int. Cl.
*A61M 16/16* (2006.01)
*A61M 16/00* (2006.01)
(Continued)

(52) U.S. Cl.
CPC ........ *A61M 16/16* (2013.01); *A61M 16/0066* (2013.01); *A61M 16/1075* (2013.01);
(Continued)

(58) Field of Classification Search
CPC .......... A61M 16/0066; A61M 16/1075; A61M 16/147; A61M 16/208; A61M 2016/0027;
(Continued)

(56) References Cited

U.S. PATENT DOCUMENTS 4,366,105 A * 12/1982 Nowacki ............. A61M 16/109
261/DIG. 65
6,095,505 A   8/2000 Miller
(Continued)

FOREIGN PATENT DOCUMENTS

CN   107013439 A  *  8/2017  .......... F04B 39/1046
JP   H04-051965 A     2/1992
(Continued)

OTHER PUBLICATIONS

Japanese Office Action for Application No. 2020-539333 dated Aug. 31, 2021.
(Continued)

*Primary Examiner* — Timothy A Stanis
*Assistant Examiner* — Tina Zhang
(74) *Attorney, Agent, or Firm* — McDonald Hopkins LLC

(57) ABSTRACT

A humidification apparatus includes a bag-shaped flexible reservoir where water is stored, a vaporizer that vaporizes supplied water, a water supply path connected to the flexible reservoir and the vaporizer, an accommodation portion where the flexible reservoir is accommodated, a pressurization source that compresses the flexible reservoir by pressurizing a space outside the flexible reservoir and inside the accommodation portion, and a controller that controls an operation of the pressurization source. Water stored in the flexible reservoir is supplied to the vaporizer through the water supply path by compressive force with which the flexible reservoir is compressed.

21 Claims, 18 Drawing Sheets

(51) Int. Cl.
*A61M 16/10* (2006.01)
*A61M 16/14* (2006.01)
*A61M 16/20* (2006.01)

(52) U.S. Cl.
CPC ........ *A61M 16/147* (2014.02); *A61M 16/208* (2013.01); *A61M 2016/0027* (2013.01); *A61M 2205/0294* (2013.01); *A61M 2205/3368* (2013.01); *A61M 2230/40* (2013.01)

(58) Field of Classification Search
CPC .. A61M 2205/0294; A61M 2205/3368; A61M 2230/40; A61M 11/005; A61M 11/042; A61M 16/0069; A61M 16/105; A61M 2016/0021; A61M 2205/7545; A61M 2016/0039; A61M 2205/3331; A61M 2205/42; A61M 2205/505; A61M 16/024; A61M 16/109; A61M 2205/07; A61M 16/16–186; B65D 83/0055; B67D 1/04; B67D 1/0425; B67D 7/0255; B67D 7/0261; F04B 43/113; F04B 43/073; F24F 6/00; F24F 2006/008; F24F 3/14; F24F 6/025

See application file for complete search history.

(56) References Cited

U.S. PATENT DOCUMENTS

| | | | | |
|---|---|---|---|---|
| 9,402,973 | B2* | 8/2016 | Phillips | A61M 25/007 |
| 10,087,062 | B2* | 10/2018 | Witte | B67D 1/0462 |
| 2005/0171512 | A1* | 8/2005 | Flaherty | A61M 5/14248 |
| | | | | 604/890.1 |
| 2008/0099017 | A1* | 5/2008 | Bordewick | A61M 16/0057 |
| | | | | 128/204.21 |
| 2010/0024816 | A1* | 2/2010 | Weinstein | A61M 16/1095 |
| | | | | 261/130 |
| 2010/0037896 | A1* | 2/2010 | Mashak | A61M 16/0081 |
| | | | | 128/205.12 |
| 2010/0065051 | A1 | 3/2010 | Potharaju et al. | |
| 2013/0263851 | A1 | 10/2013 | Arcilla et al. | |
| 2015/0165146 | A1* | 6/2015 | Bowman | A61M 16/161 |
| | | | | 128/203.14 |
| 2016/0229679 | A1* | 8/2016 | Ware | B67D 7/06 |
| 2017/0095635 | A1 | 4/2017 | Huby | |
| 2018/0214635 | A1* | 8/2018 | Raman | A61M 5/172 |
| 2018/0250490 | A1* | 9/2018 | Burgess | A61M 39/24 |
| 2019/0117512 | A1 | 4/2019 | Shirotani et al. | |

FOREIGN PATENT DOCUMENTS

| | | |
|---|---|---|
| JP | H05-312363 A | 11/1993 |
| JP | 2003-111839 A | 4/2003 |
| JP | 2010-203638 A | 9/2010 |
| JP | 2013-165757 A | 8/2013 |
| JP | 2014-508551 A | 4/2014 |
| JP | 2014-166495 A | 9/2014 |
| JP | 2017-113238 A | 6/2017 |
| JP | 2017-525513 A | 9/2017 |
| JP | 3212301 U | 9/2017 |
| JP | 2018-028366 A | 2/2018 |
| WO | 2017/104432 A1 | 6/2017 |

OTHER PUBLICATIONS

Office Action for Japanese Patent Application No. 2020-539333 dated Dec. 7, 2021 .

International Search Report for PCT/JP2019/031966 dated Nov. 5, 2019.

Written Opinion for PCT/JP2019/031966 dated Nov. 5, 2019.

\* cited by examiner

HUMIDIFICATION APPARATUS AND HUMIDIFICATION AND BLOWING APPARATUS FOR RESPIRATORY ORGANS INCLUDING THE SAME

CROSS REFERENCE TO RELATED APPLICATION

This is a continuation of International Application No. PCT/JP2019/031966 filed on Aug. 14, 2019 which claims priority from Japanese Patent Application No. 2018-160393 filed on Aug. 29, 2018. The contents of these applications are incorporated herein by reference in their entireties.

BACKGROUND

The present disclosure relates to a humidification apparatus that humidifies gas to be humidified by vaporizing water and a humidification and blowing apparatus for respiratory organs including the humidification apparatus.

Various humidification mechanisms have conventionally been invented, and an optimal humidification mechanism among them is selected for use depending on a purpose of use of an applied product. A humidification and blowing apparatus for respiratory organs represents one of a group of products to which the humidification mechanism is applied. This humidification and blowing apparatus for respiratory organs includes a continuous positive airway pressure (CPAP) apparatus, a steam inhaler, and an oxygen inhaler.

The CPAP apparatus among them is used for treatment of sleep apnea syndrome and sends air into the airway of a sleeping user. More specifically, the CPAP apparatus is provided with a blower therein and keeps sending air through an air tube to a mask attached to the nose or the mouth of the user. The CPAP apparatus may incorporate a humidification apparatus, and the CPAP apparatus incorporating the humidification apparatus humidifies air sent to the user.

For example, a CPAP apparatus disclosed in Japanese Patent Laying-Open No. 2014-166495 (PTL 1) is available as the CPAP apparatus incorporating the humidification apparatus. In the CPAP apparatus disclosed in this literature, a heater is provided under a tank where water is stored, and water stored in the tank is heated as the heater is driven. An air passage is formed such that an air current generated by a blower passes through an upper portion of the tank, so that water vapor generated by heating by the heater described above is contained in the air current and humidified air is thus sent into the airway of the user.

PTL 1: Japanese Patent Laying-Open No. 2014-166495

BRIEF SUMMARY

In the humidification apparatus incorporated in the humidification and blowing apparatus for respiratory organs represented by the CPAP apparatus described above, however, a large amount of water vapor does not have to be generated at once, whereas a small amount of water vapor should continually be generated. The humidification apparatus as disclosed in the literature is not necessarily effective from a point of view of energy efficiency.

Humidification apparatuses to be incorporated in the humidification and blowing apparatuses for respiratory organs are various in construction in addition to the construction described above. The apparatus constructions, however, are complicated, or an expensive component is included. Therefore, from a point of view of reduction in size or manufacturing cost, those constructions are far from being effective. Furthermore, most of these humidification apparatuses are poor in ease of maintenance such as cleaning of the inside of the apparatuses that should be kept clean.

Therefore, the present disclosure is made in view of the problems described above, and an object thereof is to provide a compact humidification apparatus capable of efficient humidification and a humidification and blowing apparatus for respiratory organs including the same.

A humidification apparatus based on a first aspect of the present disclosure includes a flexible reservoir, a vaporizer, a water supply path, an accommodation portion, a pressurization source, and a controller. The flexible reservoir is in a shape of a bag where water is stored. The vaporizer vaporizes supplied water. The water supply path has one end detachably connected to the flexible reservoir and the other end connected to the vaporizer. In the accommodation portion, the flexible reservoir is accommodated. The pressurization source compresses the flexible reservoir by pressurizing a space outside the flexible reservoir and inside the accommodation portion. The controller controls an operation of the pressurization source. In the humidification apparatus based on the first aspect of the present disclosure, water stored in the flexible reservoir is supplied to the vaporizer through the water supply path by compressive force with which the flexible reservoir is compressed.

In the humidification apparatus based on the first aspect of the present disclosure, preferably, the pressurization source includes an ambient air introduction source that introduces ambient air into the space outside the flexible reservoir and inside the accommodation portion.

In the humidification apparatus based on the first aspect of the present disclosure, preferably, the ambient air introduction source includes a piezoelectric pump.

In the humidification apparatus based on the first aspect of the present disclosure, the accommodation portion may be defined by a pressure bulkhead.

In the humidification apparatus based on the first aspect of the present disclosure, the accommodation portion may be defined by a bag-shaped member. In that case, preferably, the flexible reservoir and the bag-shaped member are joined and integrated with each other to be in a two-ply bag structure.

A humidification apparatus based on a second aspect of the present disclosure includes an elastic reservoir, a vaporizer, a water supply path, a valve, a valve driver, and a controller. The elastic reservoir is in a shape of a bag where water is stored. The vaporizer vaporizes supplied water. The water supply path has one end detachably connected to the elastic reservoir and the other end connected to the vaporizer. The valve is provided in the water supply path. The valve in an open state allows flow of water through the water supply path and the valve in a closed state cuts off flow of water through the water supply path. The valve driver switches the valve to any of the open state and the closed state. The controller controls an operation of the valve driver. In the humidification apparatus based on the second aspect of the present disclosure, the elastic reservoir is elastically inflated and deformed by injection of water thereinto, so that water stored in the elastic reservoir is supplied to the vaporizer through the water supply path in the open state owing to elastic resilience of the elastic reservoir.

In the humidification apparatuses based on the first and second aspects of the present disclosure, preferably, a check valve that allows movement of fluid from the water supply path toward the vaporizer and restricts movement of fluid from the vaporizer toward the water supply path is provided at the other end.

In the humidification apparatuses based on the first and second aspects of the present disclosure, preferably, a flow path defining surface and/or an end surface of the other end are/is made water repellent.

In the humidification apparatuses based on the first and second aspects of the present disclosure, preferably, an orifice is provided in the water supply path.

In the humidification apparatuses based on the first and second aspects of the present disclosure, preferably, the vaporizer includes a heater that heats supplied water.

The humidification apparatuses based on the first and second aspects of the present disclosure preferably further include a temperature detector that detects a temperature of the heater and a power consumption detector that detects power consumed by the heater. In that case, preferably, the controller controls output from the heater to maintain the temperature of the heater at a constant temperature based on the temperature detected by the temperature detector. In that case, preferably, the controller controls an amount of supply of water to the vaporizer based on power consumption detected by the power consumption detector to adjust an amount of humidification.

A humidification and blowing apparatus for respiratory organs based on the present disclosure includes a blowing apparatus including a blower that sends gas into an airway of a user and any of the humidification apparatuses based on the first and second aspects of the present disclosure. An air current generated as the blower is driven is humidified by the humidification apparatus.

The humidification and blowing apparatus for respiratory organs based on the present disclosure may further include a breathing state sensing portion that senses a breathing state of the user. In that case, preferably, the controller determines whether the user is performing an inhalation operation or an exhalation operation based on a result of sensing by the breathing state sensing portion. In that case, preferably, when the controller determines that the user is performing the inhalation operation, the humidification apparatus performs a humidification operation, and when the controller determines that the user is performing the exhalation operation, the humidification apparatus stops the humidification operation.

The humidification apparatus based on the first aspect of the present disclosure may further include a pressure sensing portion that senses a pressure in the space outside the flexible reservoir and inside the accommodation portion. In that case, preferably, the controller controls an amount of supply of water to the vaporizer based on the pressure sensed by the pressure sensing portion to adjust an amount of humidification.

According to the present disclosure, a compact humidification apparatus capable of efficient humidification and a humidification and blowing apparatus for respiratory organs including the same can be provided.

DETAILED DESCRIPTION

Figure 1:
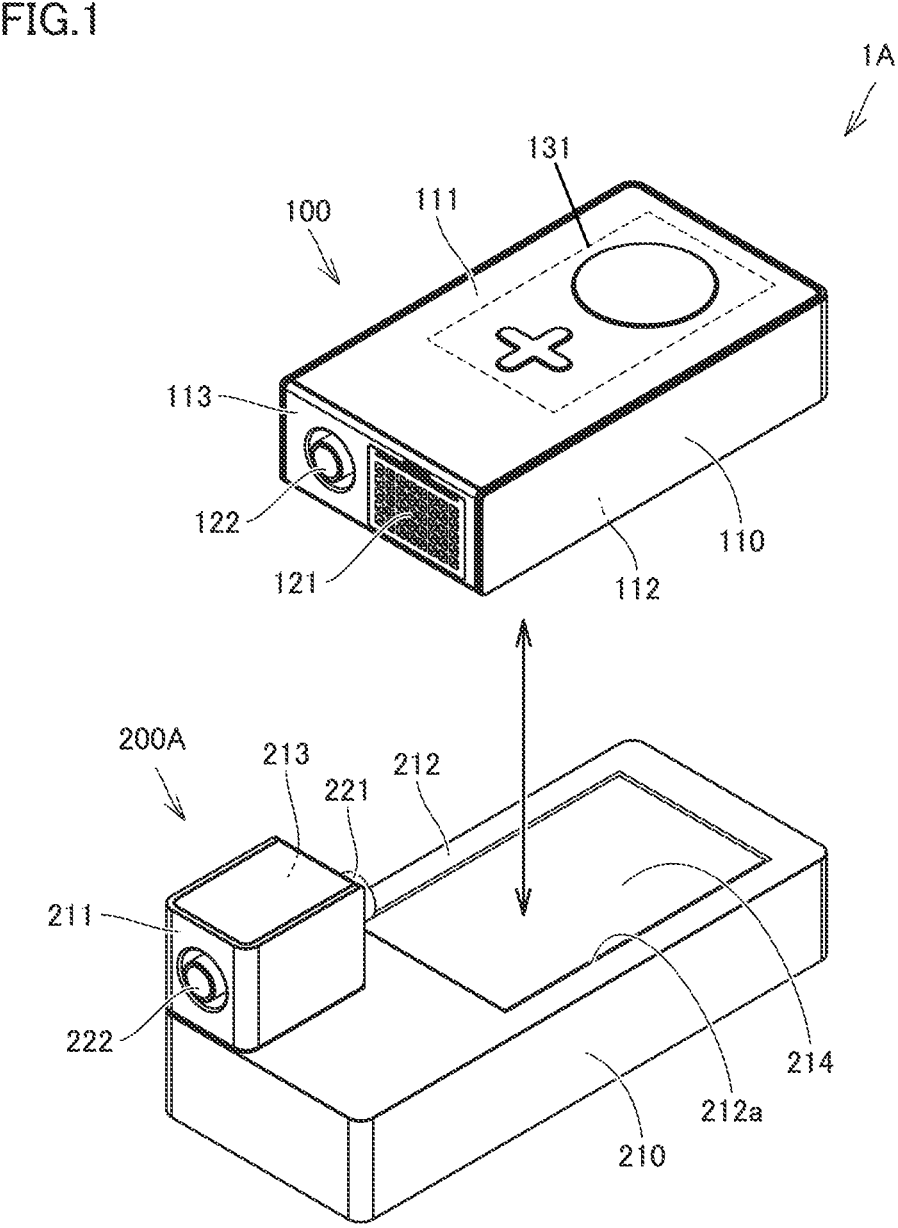
FIG. 1 is a perspective view showing a manner of attachment and detachment of a blowing unit and a humidification unit of a CPAP apparatus according to a first embodiment.

An embodiment of the present disclosure will be described in detail below with reference to the drawings. Embodiments shown below illustrate an application of the present disclosure to a CPAP apparatus as a humidification and blowing apparatus for respiratory organs and a humidification apparatus incorporated therein. In the embodiments shown below, the same or common elements in the drawings have the same reference characters allotted and description thereof will not be repeated.

First Embodiment

Figure 2:
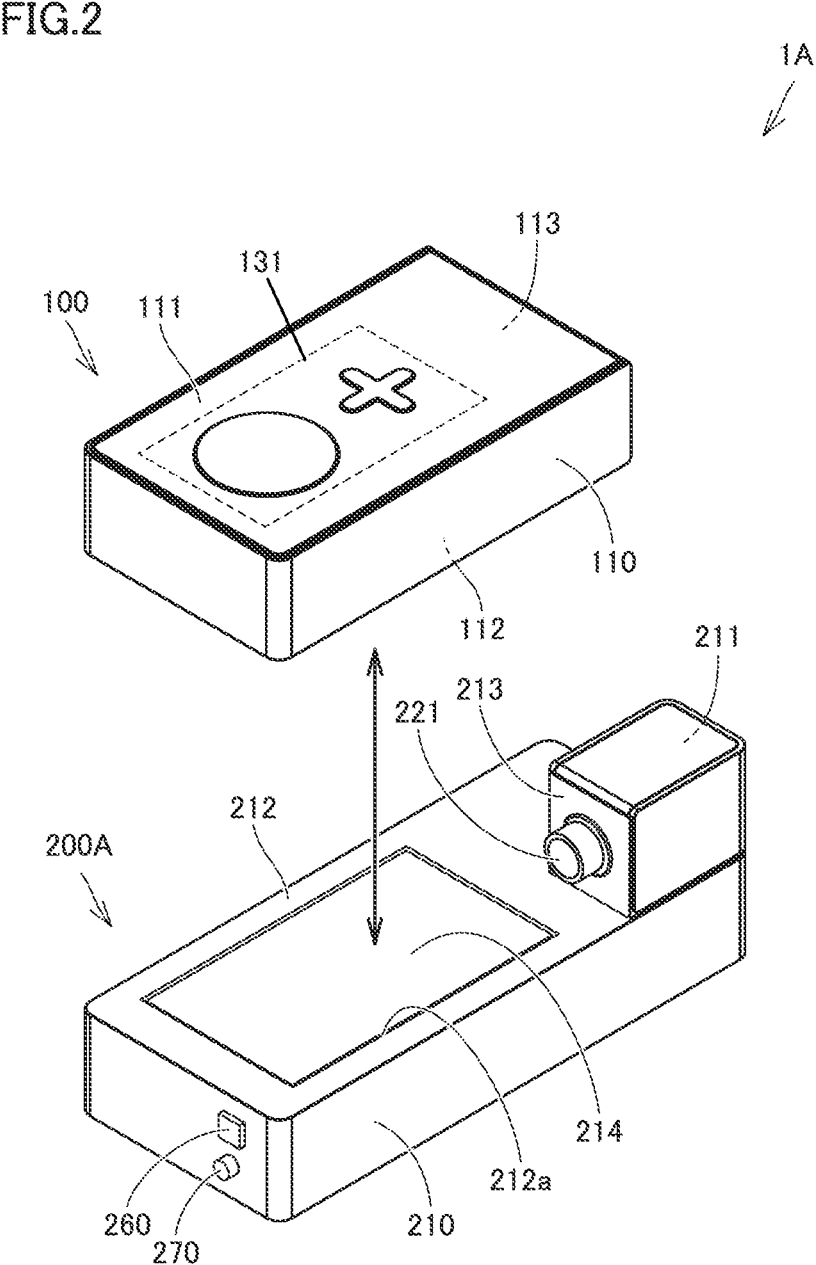
FIG. 2 is a perspective view at a different angle, of the manner of attachment and detachment shown in FIG. 1.
Figure 3:
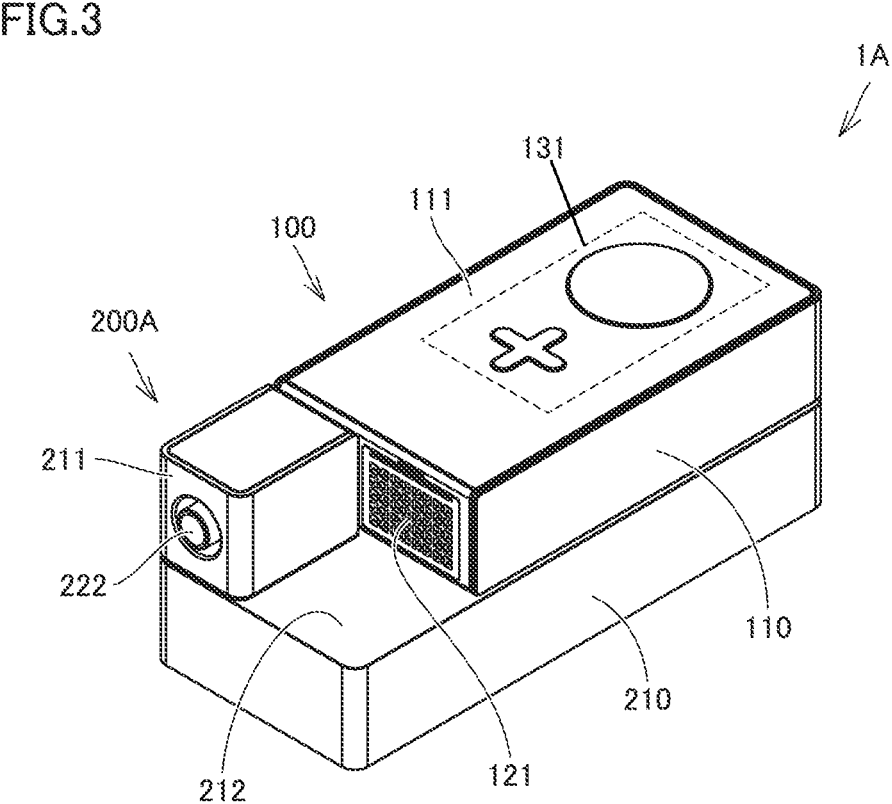
FIG. 3 is a perspective view showing a state that the blowing unit has been attached to the humidification unit in the CPAP apparatus according to the first embodiment.

FIG. 1 is a perspective view showing a manner of attachment and detachment of a blowing unit and a humidification unit of a CPAP apparatus according to a first embodiment of the present disclosure and FIG. 2 is a perspective view at a different angle, of the manner of attachment and detachment shown in FIG. 1. FIG. 3 is a perspective view showing a state that the blowing unit has been attached to the humidification unit in the CPAP apparatus according to the present embodiment. A schematic construction of a CPAP apparatus 1A according to the present embodiment and a manner of attachment and detachment thereof will initially be described with reference to FIGS. 1 to 3.

As shown in FIGS. 1 to 3, CPAP apparatus 1A includes a blowing unit 100 as a blowing apparatus and a humidification unit 200A as a humidification apparatus. Blowing unit 100 mainly includes a blower 140 (see FIGS. 5 to 7) and humidification unit 200A is mainly provided with a pressurization chamber 216 and a vaporization chamber 217 (see FIGS. 6 and 7) that make up a humidification mechanism.

Humidification unit 200A is attachable to and detachable from blowing unit 100. CPAP apparatus 1A according to the present embodiment can be used in two states of a state that humidification unit 200A is attached to blowing unit 100 and a state that humidification unit 200A is not attached to blowing unit 100.

CPAP apparatus 1A is constituted of a plurality of divided units and the plurality of units are attachable to and detachable from each other so that high convenience is exhibited not only at home but also in staying out. At home, humidification unit 200A is attached to blowing unit 100 so that CPAP apparatus 1A can be used in the first state of use described above. In staying out, CPAP apparatus 1A can be used in the second state of use described above without attaching humidification unit 200A to blowing unit 100.

In CPAP apparatus 1A according to the present embodiment, as blowing unit 100 is placed on humidification unit 200A, humidification unit 200A is attached to blowing unit 100.

Blowing unit 100 has a low-profile outer geometry substantially like a parallelepiped and has an outer shell formed from a first housing 110. First housing 110 includes an upper surface and a lower surface located as being aligned in a vertical direction during use and four side surfaces connecting the upper surface and the lower surface to each other.

The upper surface of first housing 110 defines an operation surface 111 where an operation portion 131 is provided. The lower surface of first housing 110 defines a placement surface 112 to be placed on humidification unit 200A in a first state of use which will be described later and placed on a floor surface or a table in a second state of use which will be described later. One of the four side surfaces of first housing 110 defines a first connection surface 113 connected to humidification unit 200A in the first state of use which will be described later.

Humidification unit 200A has an elongated outer geometry substantially like a parallelepiped and has an outer shell formed from a second housing 210. Second housing 210 includes an upper surface and a lower surface located as being aligned in the vertical direction during use and four side surfaces connecting the upper surface and the lower surface to each other, and a protrusion that protrudes upward is provided in one of four corners of the upper surface.

The lower surface of second housing 210 defines a placement surface to be placed on a floor surface or a table in the first state of use which will be described later. A portion except for the above-described protrusion of the upper surface of second housing 210 defines a stage surface 212 on which blowing unit 100 is carried in the first state of use which will be described later. An opening 212a is provided at a prescribed position in stage surface 212. Opening 212a communicates with pressurization chamber 216 which will be described later, and a flexible reservoir 241 (see FIGS. 5 to 7) which will be described later is put into and taken out of pressurization chamber 216 therethrough. A lid 214 is attachable to opening 212a and opening 212a is normally closed by lid 214.

One of side surfaces of the protrusion described above defines a tube connection surface 211 to which an air tube 300 (see FIGS. 4A, 4B and 5) is connected in the first state of use which will be described later and another one of the side surfaces of the protrusion described above defines a second connection surface 213 connected to blowing unit 100 in the first state of use which will be described later.

First connection surface 113 of first housing 110 is provided with a first inlet 121 for introducing air from the outside of first housing 110 and a first outlet 122 for emitting air from the inside of first housing 110.

Second connection surface 213 of second housing 210 is provided with a second inlet 221 for introducing air from the outside of second housing 210 and tube connection surface 211 of second housing 210 is provided with a second outlet 222 for emitting air from the inside of second housing 210. At prescribed positions in the side surface of second housing 210, a piezoelectric pump 260 as an ambient air introduction source for intake of air as ambient air from the outside of second housing 210 into after-mentioned pressurization chamber 216 provided inside second housing 210 and an electromagnetic valve 270 as an exhaust valve for emitting air from pressurization chamber 216 to the outside of second housing 210 are provided. Piezoelectric pump 260 as the ambient air introduction source corresponds to the pressurization source that pressurizes pressurization chamber 216.

As set forth above, while humidification unit 200A is attached to blowing unit 100 by placing blowing unit 100 on humidification unit 200A as shown in FIG. 3, placement surface 112 of first housing 110 is located as being opposed to stage surface 212 of second housing 210 and first connection surface 113 of first housing 110 is located as being opposed to second connection surface 213 of second housing 210. Therefore, first outlet 122 provided in first connection surface 113 of first housing 110 is connected to second inlet 221 provided in second connection surface 213 of second housing 210. Since first inlet 121 provided in first housing 110 is not covered with second housing 210 even in that state, the first inlet is open toward the outside.

While humidification unit 200A is not attached to blowing unit 100, first connection surface 113 of first housing 110 is exposed to the outside. Therefore, first inlet 121 and first outlet 122 provided in first connection surface 113 of first housing 110 are both open toward the outside.

Figure 4A:
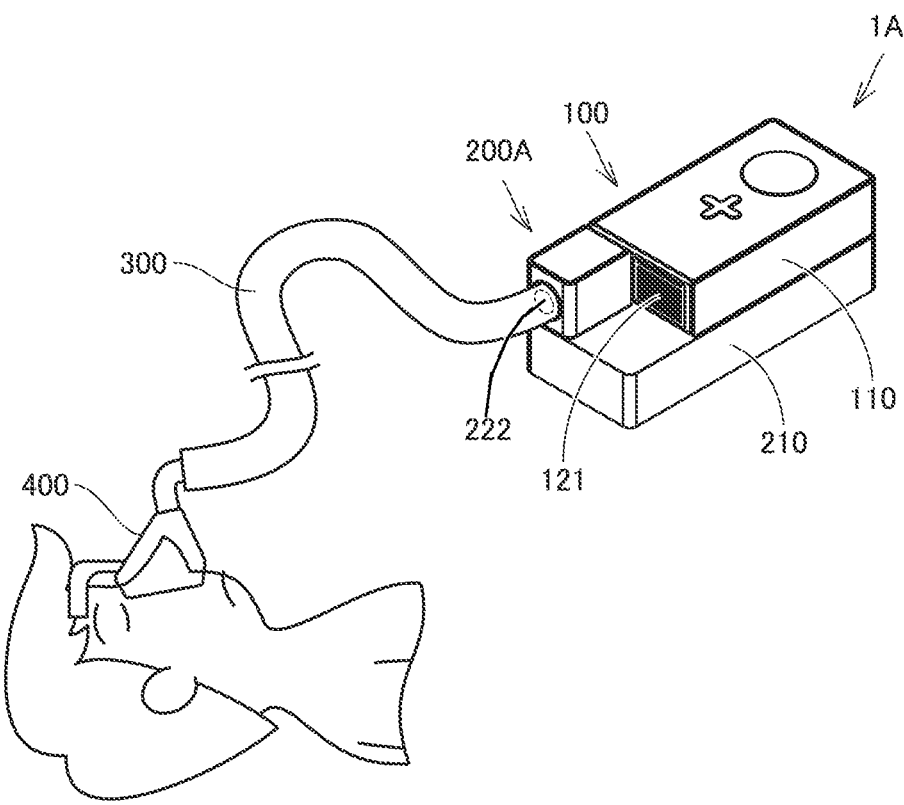
FIGS. 4A and 4B are diagrams schematically showing a first state of use and a second state of use of the CPAP apparatus according to the first embodiment.
Figure 4B:
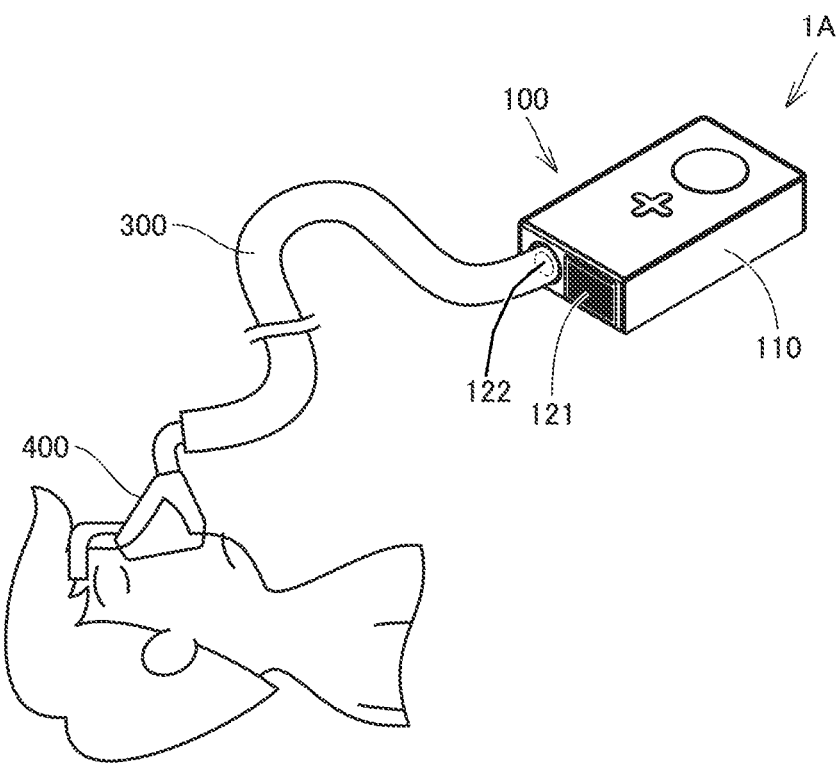

FIGS. 4A and 4B are diagrams schematically showing a state of use of the CPAP apparatus according to the present embodiment, with FIGS. 4A and 4B showing the first state of use and the second state of use, respectively. The first state of use and the second state of use of CPAP apparatus 1A according to the present embodiment will now be described with reference to FIGS. 4A and 4B.

As shown in FIG. 4A, in the first state of use, CPAP apparatus 1A is used with humidification unit 200A being attached to blowing unit 100 as described above. In that case, air tube 300 has one end connected to second outlet 222 provided in humidification unit 200A and has the other end connected to mask 400.

Though details will be described later, in the first state of use, blower 140 provided in blowing unit 100 is driven to suction air through first inlet 121 provided in blowing unit 100 into CPAP apparatus 1A and suctioned air is emitted from second outlet 222 provided in humidification unit 200A to the outside of CPAP apparatus 1A. Air emitted from second outlet 222 is thus sent into the airway of a user through air tube 300 and mask 400.

As shown in FIG. 4B, in the second state of use, CPAP apparatus 1A is used with humidification unit 200A not being attached to blowing unit 100 as described above. In that case, air tube 300 has one end connected to first outlet 122 provided in blowing unit 100 and the other end connected to mask 400.

In the second state of use, blower 140 provided in blowing unit 100 is driven to suction air through first inlet 121 provided in blowing unit 100 into CPAP apparatus 1A and suctioned air is emitted from first outlet 122 provided in blowing unit 100 to the outside of CPAP apparatus 1A. Air emitted from first outlet 122 is thus sent into the airway of the user through air tube 300 and mask 400.

Mask 400 is attached, for example, as being applied to cover the nose or the mouth of a user. Mask 400 of a shape or a structure in conformity with a user can be selected from among various types of masks, and the shape or the structure shown in FIGS. 4A and 4B are merely by way of example.

CPAP apparatus 1A is an apparatus that keeps sending air into the airway in order to open the airway to prevent apnea during sleep while sending of air is timed to coincide with breathing by the user. Therefore, in CPAP apparatus 1A, in any of the first state of use and the second state of use described above, a controller 130 (see FIG. 5) which will be described later carries out various types of control such as feedback control or feedforward control based on a flow rate and a pressure detected by a flow rate sensor 133 and a pressure sensor 134 (see FIG. 5) which will be described later. The number of revolutions of blower 140 is thus increased or decreased to adjust an amount of sent air, so that the user is prevented from falling into apnea during sleep.

CPAP apparatus 1A according to the present embodiment is mainly characterized by humidification unit 200A as the humidification apparatus. Therefore, of the first state of use and the second state of use described above, description will be given below, with focus being placed on the first state of use in which humidification unit 200A is used in addition to blowing unit 100, and description of the second state of use in which only blowing unit 100 is used without using humidification unit 200A is not provided.

Figure 5:
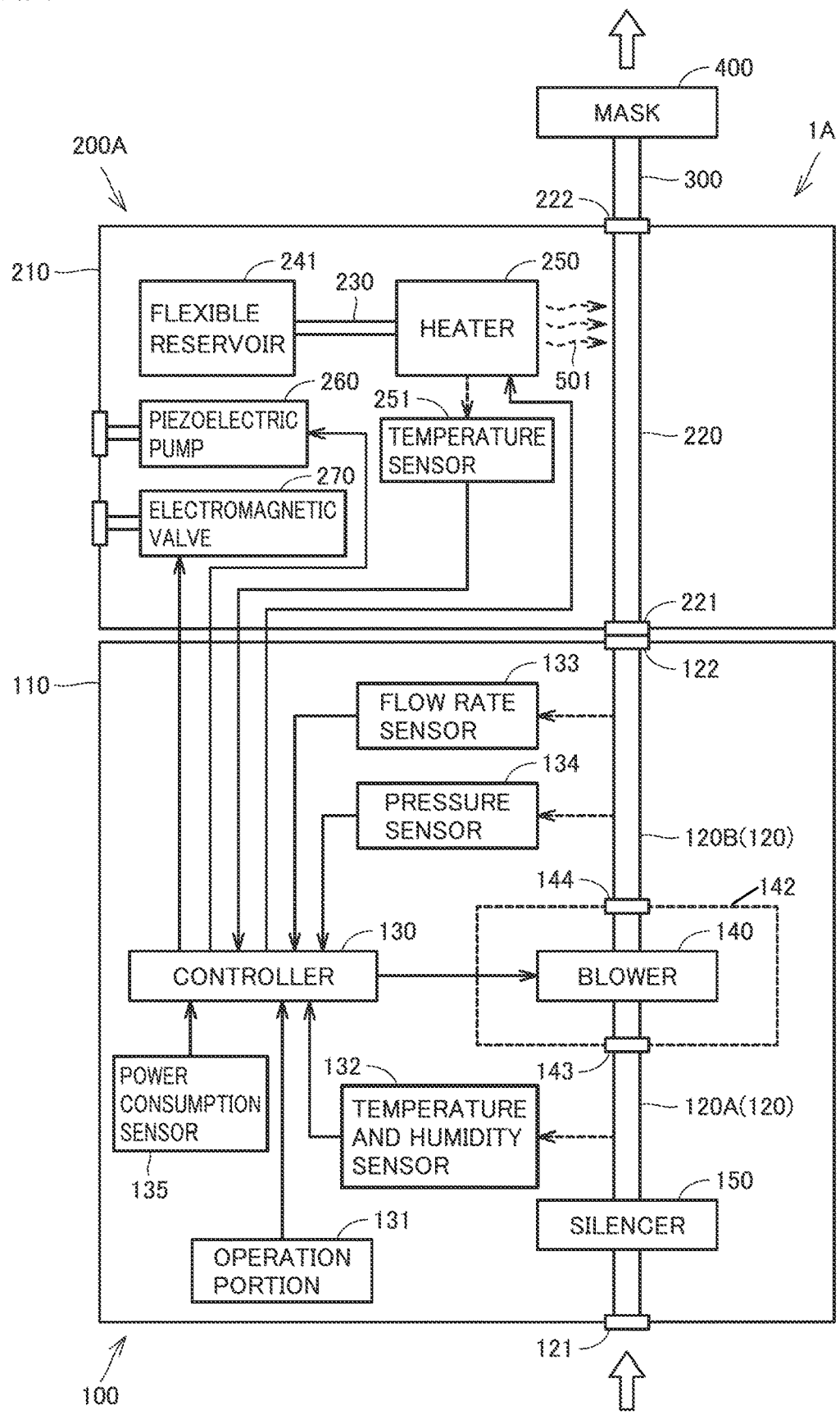
FIG. 5 is a diagram showing a configuration of a functional block in the first state of use of the CPAP apparatus according to the first embodiment.

FIG. 5 is a diagram showing a configuration of a functional block in the first state of use of the CPAP apparatus according to the present embodiment. The configuration of the functional block in the first state of use of CPAP apparatus 1A according to the present embodiment will now be described with reference to FIG. 5.

As shown in FIG. 5, CPAP apparatus 1A includes controller 130, operation portion 131, a temperature and humidity sensor 132, flow rate sensor 133, pressure sensor 134, power consumption sensor 135, blower 140, a silencer 150, a flexible reservoir 241, a heater 250, a temperature sensor 251, piezoelectric pump 260, and electromagnetic valve 270. Among these, controller 130, operation portion 131, temperature and humidity sensor 132, flow rate sensor 133, pressure sensor 134, power consumption sensor 135, blower 140, and silencer 150 are provided in blowing unit 100. Flexible reservoir 241 is accommodated in after-mentioned pressurization chamber 216 provided in humidification unit 200A. Heater 250, temperature sensor 251, piezoelectric pump 260, and electromagnetic valve 270 are provided in humidification unit 200A. Humidification unit 200A is also provided with a water supply path 230 which will be described later.

First housing 110 of blowing unit 100 is provided with a first flow path 120 in addition to first inlet 121 and first outlet 122 described above. First flow path 120 connects first inlet 121 and first outlet 122 to each other.

First flow path 120 is provided with blower 140. For example, a centrifugal fan is adopted as blower 140. Blower 140 is provided in an after-mentioned blower chamber 117 (see FIGS. 6 and 7) provided in first housing 110, and thus arranged over first flow path 120.

Blower 140 includes a casing 142, and casing 142 is provided with a suction port 143 and an emission port 144 of blower 140. Therefore, first flow path 120 includes an upstream flow path portion 120A that connects first inlet 121 provided in first housing 110 and suction port 143 provided in blower 140 to each other and a downstream flow path portion 120B that connects emission port 144 provided in blower 140 and first outlet 122 provided in first housing 110 to each other.

Upstream flow path portion 120A which is a portion of first flow path 120 located between first inlet 121 and suction port 143 is provided with silencer 150. Silencer 150 suppresses leakage of noise (operating noise of a drive motor provided in blower 140 or wind noise) generated in blower 140 to the outside through first inlet 121, details of which will be described later.

Second housing 210 of humidification unit 200A is provided with a second flow path 220 in addition to second inlet 221 and second outlet 222 described above. Second flow path 220 connects second inlet 221 and second outlet 222 to each other.

In second flow path 220, a humidification mechanism which will be described later humidifies air that passes therethrough. In the first state of use, moderate moisture (that is, water vapor 501 shown with a wavy dashed arrow in a figure) is thus provided to air sent toward the airway of a user.

Water supply path 230 is provided in humidification unit 200A as described above. Water supply path 230 connects flexible reservoir 241 and heater 250 as the vaporizer to each other, and serves to send water stored in flexible reservoir 241 to heater 250. Flexible reservoir 241 is formed from a bag-shaped member where water is stored, and it is attachable to and detachable from water supply path 230.

Heater 250 serves to vaporize supplied water by heating the same. Piezoelectric pump 260 is an air pump that delivers air. Though details of piezoelectric pump 260 will be described later, the piezoelectric pump serves to take in air outside humidification unit 200A and to pressurize pressurization chamber 216 which will be described later. Though details of electromagnetic valve 270 will be described later, the electromagnetic valve serves to emit air in pressurization chamber 216 to the outside of humidification unit 200A and to reduce a pressure in pressurization chamber 216.

Controller 130 includes, as its main constituent elements, a central processing unit (CPU) that executes a program, a read only memory (ROM)/random access memory (RAM), driving units that drive blower 140, heater 250, piezoelectric pump 260, and electromagnetic valve 270, respectively, and a computing unit that performs various types of computation based on various types of information provided from temperature and humidity sensor 132, flow rate sensor 133, pressure sensor 134, power consumption sensor 135, and temperature sensor 251. The ROM/RAM includes a ROM that stores data in a non-volatile manner and a RAM that stores in a volatile manner, data generated as a result of execution of the program by the CPU or data provided through operation portion 131. The constituent elements of controller 130 are connected to one another through a data bus.

Processing in the CPU is performed by hardware and software executed by the CPU. Such software is stored in advance in the ROM/RAM. Software also allows acceptance of an operation onto operation portion 131, control of the drive motor that drives blower 140, control of heater 250, control of piezoelectric pump 260, control of electromagnetic valve 270, and various types of computation described above.

Controller 130, blower 140, heater 250, piezoelectric pump 260, and electromagnetic valve 270 are supplied with electric power by a not-shown internal power supply or a not-shown external power supply. For example, a not-shown alternating current (AC) adapter is used for connection with the external power supply.

Temperature and humidity sensor 132 is a sensor for measuring a temperature and a humidity of air introduced from the outside of CPAP apparatus 1A and subsequently sent into the airway of a user, and it is provided in upstream flow path portion 120A in first flow path 120. The temperature and the humidity of air detected by temperature and humidity sensor 132 is provided to controller 130 and mainly used for a humidification operation by the humidification mechanism.

Flow rate sensor 133 is a sensor for measuring a flow rate of air between CPAP apparatus 1A and air tube 300, and pressure sensor 134 is a sensor for measuring a pressure of air sent from blower 140. Flow rate sensor 133 and pressure sensor 134 correspond to the breathing state sensing portion and both of them are provided in downstream flow path portion 120B in first flow path 120.

Though detailed description is not provided, the flow rate and the pressure detected by flow rate sensor 133 and pressure sensor 134 are provided to controller 130 and controller 130 carries out control such as feedback control or feedforward control based on the flow rate and the pressure to increase or decrease the number of revolutions of blower 140. The flow rate and the pressure of air detected by flow rate sensor 133 and pressure sensor 134 are used also for the humidification operation by the humidification mechanism.

Power consumption sensor 135 is a sensor for measuring electric power supplied to heater 250, and it includes, for example, a current monitor. Power consumption detected by power consumption sensor 135 is provided to controller 130 and used mainly for the humidification operation by the humidification mechanism.

Temperature sensor 251 is a sensor for measuring a temperature of heater 250 and provided adjacently to heater 250. The temperature of heater 250 detected by temperature sensor 251 is provided to controller 130 and used mainly for the humidification operation by the humidification mechanism.

CPAP apparatus 1A may separately be provided with a display implemented by a liquid crystal display (LCD) or an organic electro-luminescence (EL) display. The display may be provided in blowing unit 100 or humidification unit 200A. Operation portion 131 does not have to be provided as a button in a physical shape as shown in FIGS. 1 to 3 but may be implemented, for example, by a touch panel provided on a display surface of the LCD. A button in operation portion 131 other than a button to switch ON and OFF the power supply of CPAP apparatus 1A may be provided in humidification unit 200A.

As shown in FIG. 5, in the first state of use, first outlet 122 provided in first housing 110 and second inlet 221 provided in second housing 210 are connected to each other. In the first state of use, second flow path 220 is thus connected to a downstream side of first flow path 120.

Therefore, in the first state of use, as blower 140 is driven, air suctioned through first inlet 121 passes through first flow path 120 and second flow path 220 in this order and is emitted from second outlet 222. Air emitted from second outlet 222 is thereafter sent into the airway of a user through air tube 300 and mask 400. In the first state of use, first inlet 121 functions as an air intake port through which air is suctioned into the inside of CPAP apparatus 1A and second outlet 222 functions as an exhaust port through which air is emitted from the inside of CPAP apparatus 1A.

Figure 6:
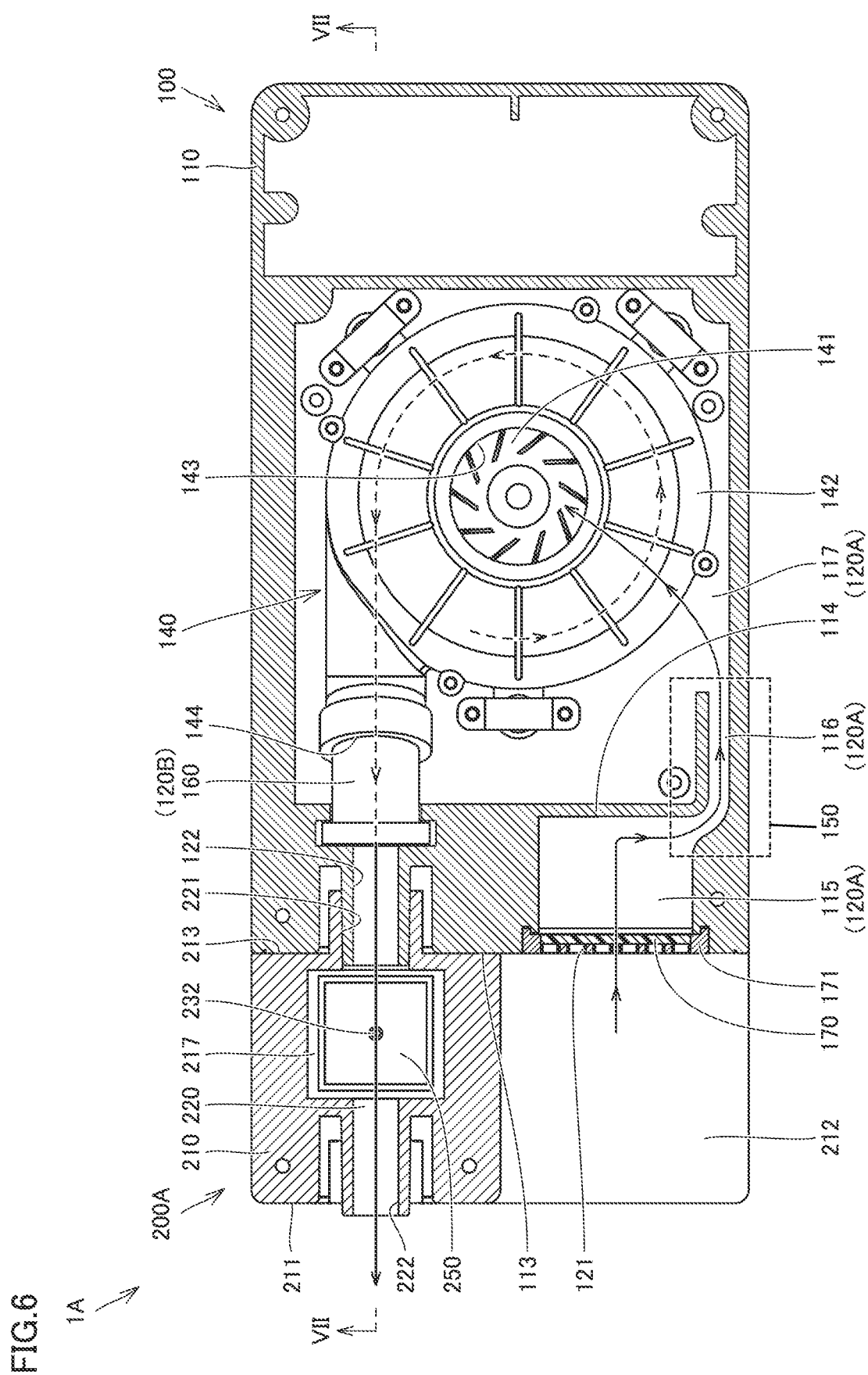
FIG. 6 is a schematic cross-sectional view in the first state of use of the CPAP apparatus according to the first embodiment.
Figure 7:
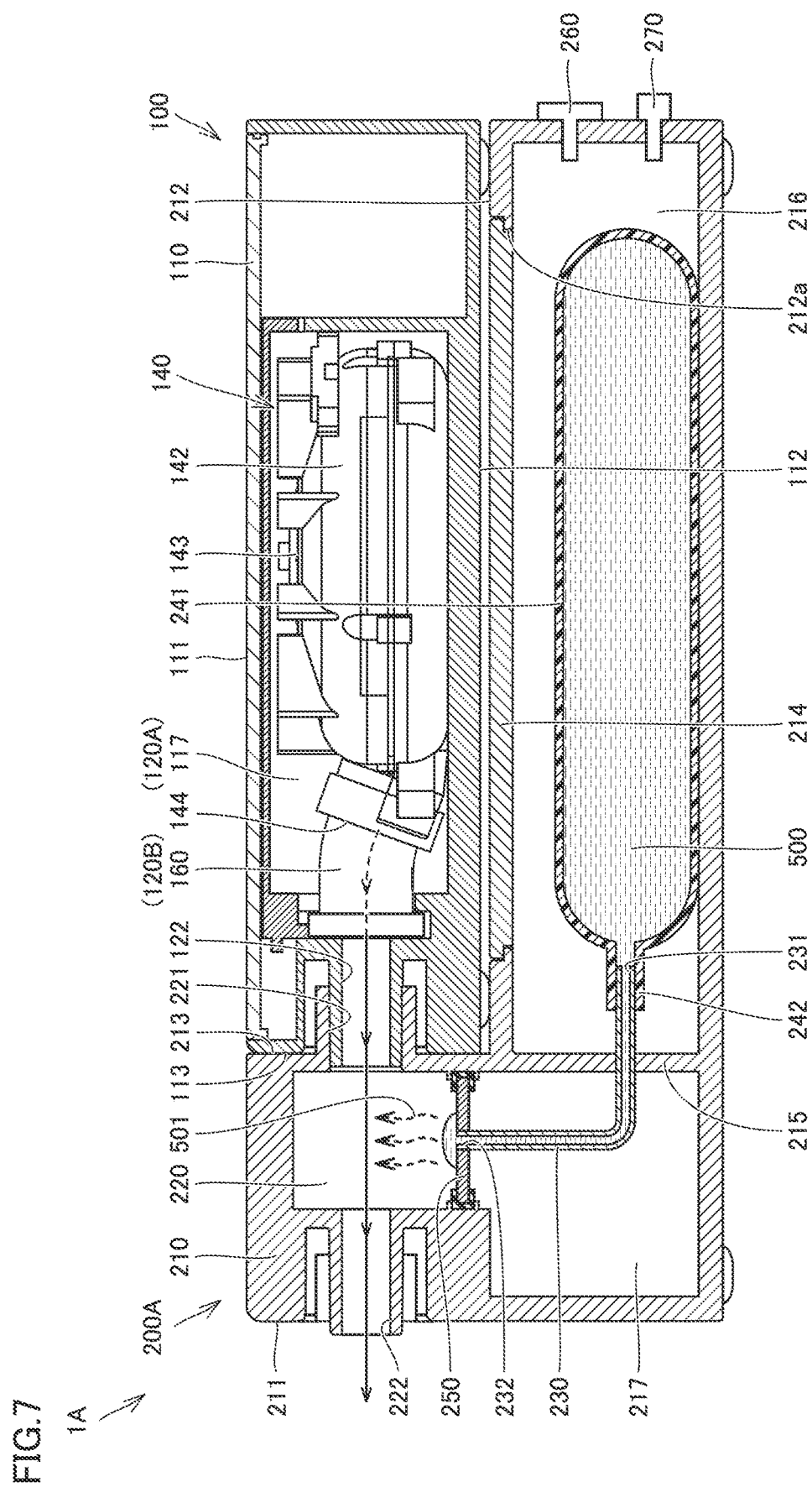
FIG. 7 is a schematic cross-sectional view along the line VII-VII shown in FIG. 6.

FIG. 6 is a schematic cross-sectional view in the first state of use of the CPAP apparatus according to the present embodiment and FIG. 7 is a schematic cross-sectional view along the line VII-VII shown in FIG. 6. A detailed structure of CPAP apparatus 1A according to the present embodiment and a flow of air in the inside of CPAP apparatus 1A in the first state of use will be described below with reference to FIGS. 6 and 7. FIGS. 6 and 7 schematically show a flow of air generated by an operation of blower 140 with an arrow.

As shown in FIGS. 6 and 7, a space within first housing 110 of blowing unit 100 is divided into a plurality of chambers by providing various walls or hoses. The plurality of chambers include a wide portion 115, a narrow portion 116, and a blower chamber 117, and wide portion 115, narrow portion 116, and blower chamber 117 correspond to upstream flow path portion 120A described above.

As shown in FIG. 6, wide portion 115 is provided adjacently to first inlet 121 provided in first connection surface 113 of first housing 110. A cross-sectional area of wide portion 115 orthogonal to a direction of flow of air is relatively large to reduce pressure loss that may be caused at first inlet 121. The cross-sectional area of wide portion 115 orthogonal to the direction of flow of air is larger than a cross-sectional area of after-mentioned narrow portion 116 orthogonal to the direction of flow of air.

At first inlet 121, a filter 170 for catching a foreign matter such as dust contained in air is provided, and a filter cover 171 that defines a part of first housing 110 is attached to first connection surface 113 in order to fix filter 170 to first connection surface 113. Filter cover 171 is provided with a plurality of holes in rows and columns, and the plurality of holes define first inlet 121.

Narrow portion 116 is provided adjacently to wide portion 115. Narrow portion 116 is defined by providing a bulkhead 114 in first housing 110, and the cross-sectional area thereof orthogonal to the direction of flow of air is relatively small. The cross-sectional area of narrow portion 116 orthogonal to the direction of flow of air is smaller than the cross-sectional area of above-described wide portion 115 orthogonal to the direction of flow of air.

Blower chamber 117 is provided adjacently to narrow portion 116, and blower 140 is accommodated therein. A cross-sectional area of blower chamber 117 orthogonal to the direction of flow of air is relatively large, and blower chamber 117 is provided as a relatively large space that occupies a most part of first housing 110. The cross-sectional area of blower chamber 117 orthogonal to the direction of flow of air is larger than the cross-sectional area of above-described narrow portion 116 orthogonal to the direction of flow of air.

First flow path 120 in a portion corresponding to wide portion 115, narrow portion 116, and blower chamber 117 is a portion where the cross-sectional area orthogonal to the direction of flow of air is abruptly increased and decreased from the downstream side toward the upstream side in the direction of flow of air, and this portion functions as silencer 150 described above. By providing silencer 150 as such, noise generated in blower 140 is attenuated by irregular reflection while it passes through silencer 150, and consequently, leakage of noise through first inlet 121 can be suppressed.

As shown in FIGS. 6 and 7, for example, a centrifugal fan is adopted as blower 140, and blower 140 is fixed to a wall (that is, a bottom plate) that defines placement surface 112 of first housing 110 while the blower is accommodated in blower chamber 117. Blower 140 includes an impeller 141, a not-shown drive motor, and casing 142.

Impeller 141 is fixed to a rotation shaft of the drive motor so that it rotates as the drive motor is driven. As impeller 141 rotates, air is agitated and centrifugal force is provided to air. An air current is thus generated in casing 142, air is suctioned through suction port 143 provided in casing 142, and air is emitted through emission port 144 provided in casing 142.

Suction port 143 of blower 140 is provided in a part of casing 142 located above the shaft portion of impeller 141 and arranged as being opposed at a distance to an inner surface of a wall (that is, a top plate) that defines operation surface 111 of first housing 110. When viewed along the shaft portion of impeller 141, emission port 144 of blower 140 is provided in a part of casing 142 located in a tangential direction of an outer edge of impeller 141 and arranged at a prescribed distance from impeller 141.

Suction port 143 of blower 140 communicates with blower chamber 117. Emission port 144 of blower 140 is provided across blower chamber 117, and has one end connected to the other end of a hose 160 connected to first outlet 122 provided in first housing 110. A space inside hose 160 corresponds to downstream flow path portion 120B described above.

First outlet 122 is provided in first connection surface 113 of first housing 110. First outlet 122 is in a shape like a nozzle such that second inlet 221 provided in second connection surface 213 of second housing 210 and air tube 300 can both be connected thereto.

As shown in FIGS. 6 and 7, the space inside second housing 210 of humidification unit 200A is divided into pressurization chamber 216 and vaporization chamber 217 by providing a partition wall 215. A part of vaporization chamber 217 of these chambers corresponds to second flow path 220 described above.

Pressurization chamber 216 is defined by the wall of second housing 210 including partition wall 215, and it is a portion where flexible reservoir 241 is accommodated. Walls of second housing 210 including partition wall 215 that define pressurization chamber 216 correspond to the accommodation portion where flexible reservoir 241 is accommodated, and each of them is provided as a pressure bulkhead. Therefore, even when pressurization chamber 216 is pressurized, the walls can maintain an internal pressure. Piezoelectric pump 260 and electromagnetic valve 270 are assembled to the wall of second housing 210 that defines pressurization chamber 216.

A diaphragm pump making use of electrostriction of a piezoelectric body in a form of a thin plate is adopted as piezoelectric pump 260, and piezoelectric pump 260 is an air pump capable of suctioning air and delivering air as described above. Piezoelectric pump 260 is provided such that a suction port thereof faces the outside of second housing 210 and an emission port thereof faces pressurization chamber 216 provided inside second housing 210, so that pressurization chamber 216 can be pressurized by taking ambient air into pressurization chamber 216.

A diaphragm valve making use of electrostriction of a piezoelectric body in a form of a thin plate is adopted as electromagnetic valve 270, and electromagnetic valve 270 is provided in a prescribed wall of second housing 210 so as to be able to emit air in pressurization chamber 216 to the outside of humidification unit 200A and to reduce a pressure in pressurization chamber 216. Electromagnetic valve 270 is preferably provided to allow pressure reduction in pressurization chamber 216 prior to detachment of lid 214 from a point of view of securing safety in operating lid 214 in taking flexible reservoir 241 out of pressurization chamber 216.

Pressurization chamber 216 is located below opening 212a provided in stage surface 212 which is the upper surface of second housing 210 and communicates with opening 212a. Opening 212a is closed by lid 214 as described above. Between a wall surface of second housing 210 that defines opening 212a and lid 214, a not-shown sealing material (gasket) for securing hermeticity in that portion is provided.

Flexible reservoir 241 is formed from a bag-shaped member where water 500 is stored, and includes a connection port 242 through which stored water 500 can be emitted. Flexible reservoir 241 is formed from a soft member that is freely deformable without allowing leakage of water 500 stored therein, and accommodated in pressurization chamber 216 described above such that it can be put into and taken out of pressurization chamber 216. Connection port 242 provided in flexible reservoir 241 is detachably connected to a connection port 231 of water supply path 230 which will be described later. Flexible reservoir 241 is formed, for example, from a resin member or a metal member like a film.

Flexible reservoir 241 is preferably disposable from a point of view of hygiene, and it may be disposed of after it is used a plurality of times or once. In an example where the flexible reservoir is disposed of after it is used a plurality of times, preferably, the flexible reservoir can readily be refilled with water 500 after water 500 is completely drained.

Vaporization chamber 217 is defined by the walls of second housing 210 including partition wall 215, and provided to include in a part thereof, the above-described protrusion provided on the upper surface of second housing 210. Water supply path 230 and heater 250 are arranged in vaporization chamber 217. Heater 250 is provided in a lower portion in the space inside the protrusion described above, to divide vaporization chamber 217 into a space above heater 250 and a space below heater 250. The space above heater 250 corresponds to second flow path 220 described above.

The space above heater 250 corresponding to second flow path 220 communicates with first flow path 120 provided inside first housing 110 through second inlet 221 provided in second connection surface 213 of second housing 210 and first outlet 122 provided in first connection surface 113 of first housing 110. The space above heater 250 corresponding to second flow path 220 communicates with second outlet 222 provided in tube connection surface 211 of second housing 210. Second outlet 222 is in a shape of a nozzle such that air tube 300 can be connected thereto.

Water supply path 230 is defined by a pipe bent substantially in an L shape, and one end thereof is provided to pass through partition wall 215 to reach pressurization chamber 216 and the other end thereof is connected to heater 250 from below. Heater 250 includes a heating plate and the other end of water supply path 230 is arranged to pass through the heating plate to face second flow path 220 described above.

Above-described one end of water supply path 230 corresponds to connection port 231 detachably connected to flexible reservoir 241 accommodated in pressurization chamber 216 and above-described the other end of water supply path 230 corresponds to a drain outlet 232 through which water 500 fed to water supply path 230 through connection port 231 is drained toward heater 250. Connection port 231 described above corresponds to a water feed port through which water 500 stored in flexible reservoir 241 is fed toward water supply path 230.

Pressurization chamber 216, water supply path 230, flexible reservoir 241, heater 250, and piezoelectric pump 260 described above mainly correspond to the humidification mechanism that humidifies gas to be humidified sent by blower 140. The humidification operation by the humidification mechanism is performed as piezoelectric pump 260 is driven for a prescribed time period.

More specifically, by adopting the construction described above, pressurization chamber 216 is defined as a hermetically sealed space. Therefore, as piezoelectric pump 260 is driven, ambient air is taken into pressurization chamber 216 and pressurization chamber 216 is pressurized. An internal pressure in the space outside flexible reservoir 241 and inside the accommodation portion thus increases, and flexible reservoir 241 is accordingly compressed.

With this compressive force, water 500 stored in flexible reservoir 241 is introduced into water supply path 230 through connection ports 242 and 231, and thereafter pushed out of water supply path 230 through drain outlet 232 and supplied to heater 250. Water supplied to heater 250 is immediately heated and vaporized by heater 250 to become water vapor 501, and water vapor is provided to air that passes through second flow path 220.

At this time, a duration for which piezoelectric pump 260 is driven is determined based on a result of detection by power consumption sensor 135 that detects power consumed by heater 250. As will be described later, in CPAP apparatus 1A according to the present embodiment, controller 130 controls output from heater 250 so as to maintain a temperature of heater 250 at a predetermined set temperature. Therefore, as water 500 is supplied to heater 250 and heat of heater 250 is used for evaporation of water 500, output from heater 250 relatively increases, and accordingly power consumed by heater 250 temporarily increases.

Since this increase in power consumed by heater 250 is basically in proportion to an amount of humidification (an amount of evaporation) with water 500, the amount of humidification can be estimated by detecting power consumption. Therefore, humidification in a necessary amount can be carried out by stopping drive of piezoelectric pump 260 at the time point when a corresponding amount of consumed power corresponding to a target amount of humidification which will be described later is reached after start of the humidification operation. By setting a thermal capacity of heater 250 to be smaller, the amount of humidification can more minutely be estimated. Therefore, for example, a film heater is preferably employed as heater 250.

As set forth above, in the first state of use, air suctioned through first inlet 121 is emitted from second outlet 222 through first flow path 120 and second flow path 220 in this order as described above, and sent into the airway of a user through air tube 300 connected to second outlet 222 and mask 400 connected to air tube 300. By this time, air has moderately been humidified by being provided with water vapor 501 in second flow path 220, and air is sent into the airway of the user.

Figure 8:
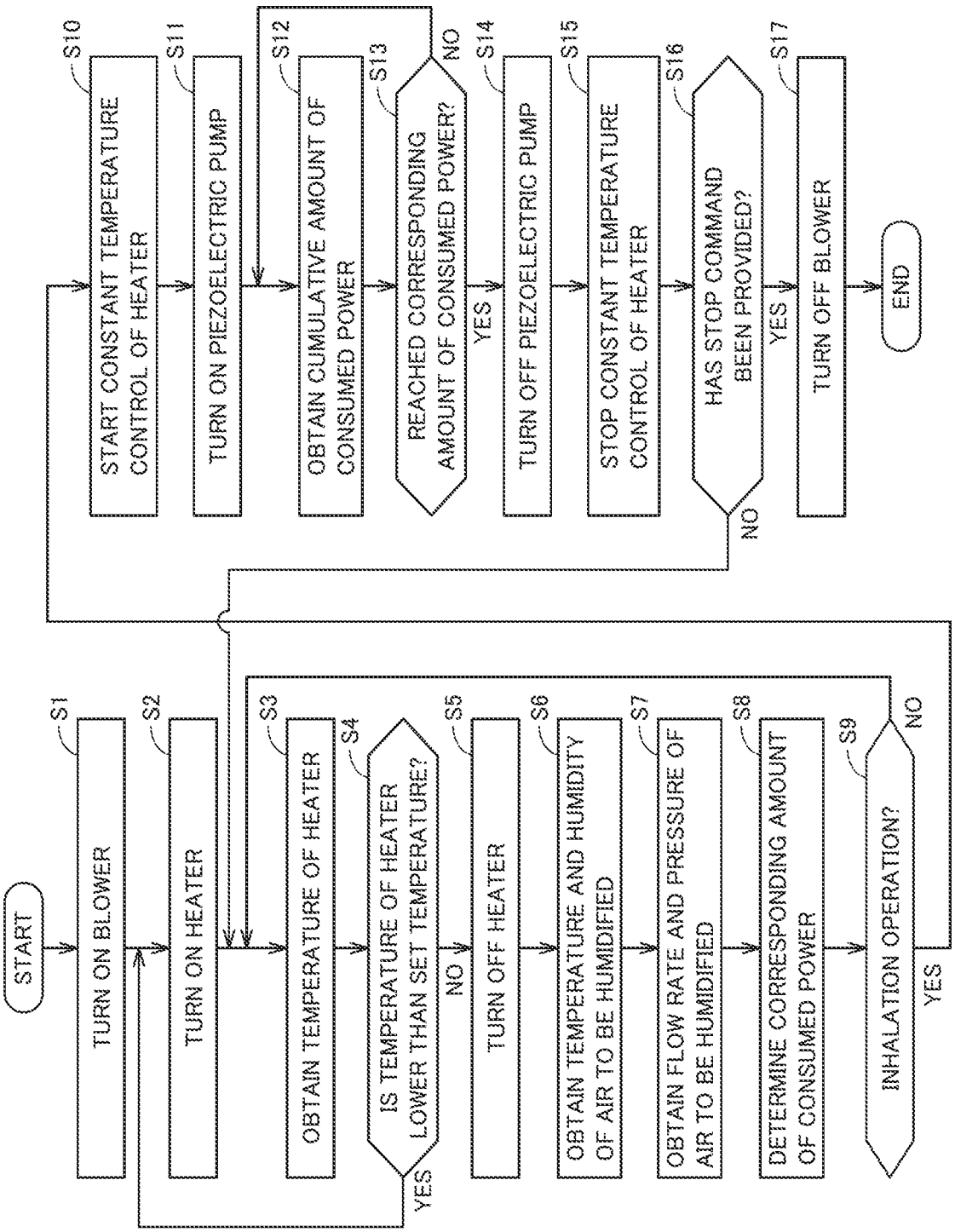
FIG. 8 is a flowchart showing an operation of a controller in the first state of use of the CPAP apparatus according to the first embodiment.
Figure 9:
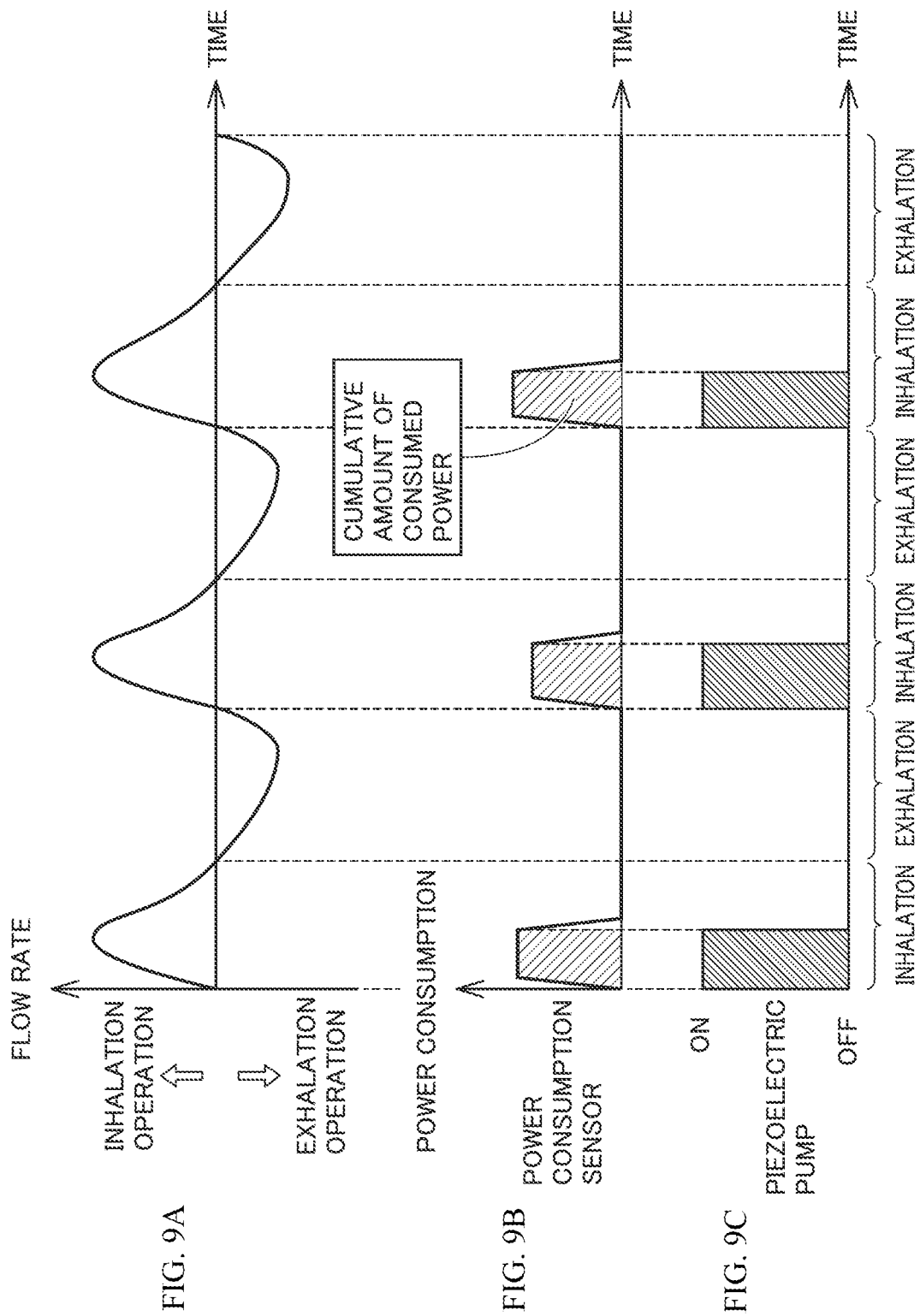
FIGS. 9A, 9B, and 9C are timing charts for illustrating a humidification operation by the CPAP apparatus according to the first embodiment.

FIG. 8 is a flowchart showing an operation of the controller in the first state of use of the CPAP apparatus according to the present embodiment. FIGS. 9A, 9B and 9C are timing charts for illustrating the humidification operation by the CPAP apparatus according to the present embodiment. Details of the humidification operation by CPAP apparatus 1A according to the present embodiment will now be described with reference to FIGS. 8, 9A, 9B, and 9C.

Referring to FIG. 8, as the user operates operation portion 131 of CPAP apparatus 1A to start use thereof, initially, controller 130 provides a drive command to blower 140 in step S1. Blower 140 is thus driven to be turned ON.

Then, in step S2, controller 130 provides a drive command to heater 250. Heater 250 is thus driven to be turned ON, and a temperature of heater 250 starts to increase.

Then, in step S3, controller 130 obtains the temperature of heater 250. Specifically, controller 130 obtains the temperature detected by temperature sensor 251 annexed to heater 250.

Then, in step S4, controller 130 determines whether or not the temperature of heater 250 is lower than a set temperature set in advance. When controller 130 determines the temperature of heater 250 as being lower than the set temperature (YES in step S4), the process proceeds to step S2 and controller 130 continues drive of heater 250. When controller 130 determines the temperature of heater 250 as not being lower than the set temperature (NO in step S4), the process proceeds to step S5. Though the set temperature of heater 250 is not particularly limited, it is set preferably to 60° C. or higher and further preferably to 80° C. or higher such that water 500 supplied to heater 250 is immediately heated and vaporized.

In step S5, controller 130 provides a drive stop command to heater 250. Drive of heater 250 is thus stopped and the heater is turned OFF.

Then, in step S6, controller 130 obtains a temperature and a humidity of air to be humidified. Specifically, controller 130 obtains the temperature and the humidity of air to be humidified detected by temperature and humidity sensor 132 provided in upstream flow path portion 120A in first flow path 120.

Then, in step S7, controller 130 obtains a flow rate and a pressure of air to be humidified. Specifically, controller 130 obtains the flow rate and the pressure of air to be humidified detected by flow rate sensor 133 and pressure sensor 134 provided in downstream flow path portion 120B in first flow path 120.

Then, in step S8, controller 130 determines a corresponding amount of consumed power. This determination is based on the temperature and the humidity of air to be humidified detected by temperature and humidity sensor 132 described above and the flow rate and the pressure (in particular, the flow rate) of air to be humidified detected by flow rate sensor 133 and pressure sensor 134 described above. For example, the ROM described above stores a data table where correlation between the temperature, the humidity, the flow rate, and the pressure of air to be humidified and the corresponding amount of consumed power corresponding to an optimal amount of humidification in accordance therewith is determined in advance, and controller 130 determines the corresponding amount of consumed power by referring to the data table.

Then, in step S9, controller 130 determines whether or not a user is performing an inhalation operation. This determination is based on the flow rate and the pressure detected by flow rate sensor 133 and pressure sensor 134 described above. When controller 130 determines that the user is not performing the inhalation operation (that is, the user is performing the exhalation operation) (NO in step S9), it resets the corresponding amount of consumed power determined in step S8, and thereafter the process proceeds to step S3 and returns to obtainment of the temperature of heater 250. When controller 130 determines that the user is performing the inhalation operation (YES in step S9), the process proceeds to step S10.

In step S10, controller 130 starts constant temperature control of heater 250. Constant temperature control of heater 250 refers to control of output from heater 250 by controller 130 so as to maintain the temperature of heater 250 at the predetermined set temperature.

Then, in step S11, controller 130 provides a drive command to piezoelectric pump 260. Piezoelectric pump 260 is thus driven to be turned ON, and supply of water 500 stored in flexible reservoir 241 to heater 250 through water supply path 230 is started.

Then, in step S12, controller 130 obtains a cumulative amount of power consumed by heater 250 from the time point of start of drive of piezoelectric pump 260. Specifically, while controller 130 obtains the amount of consumed power detected by power consumption sensor 135, it calculates the cumulative amount of consumed power by computation based thereon.

Then, in step S13, controller 130 determines whether or not the cumulative amount of consumed power has reached the corresponding amount of consumed power. When controller 130 determines that the cumulative amount of consumed power has not reached the corresponding amount of consumed power (NO in step S13), the process proceeds to step S12 and controller 130 calculates again the cumulative amount of consumed power. When controller 130 determines that the cumulative amount of consumed power has reached the corresponding amount of consumed power (YES in step S13), the process proceeds to step S14.

In step S14, controller 130 provides a drive stop command to piezoelectric pump 260. Drive of piezoelectric pump 260 is thus stopped and the piezoelectric pump is turned OFF, so that supply of water 500 stored in flexible reservoir 241 to heater 250 through water supply path 230 is stopped.

Then, in step S15, controller 130 stops constant temperature control of heater 250.

Then, in step S16, controller 130 determines whether or not a stop command to CPAP apparatus 1A has been provided. This determination is made specifically based on whether or not a command to stop use thereof has been provided by an operation by the user onto operation portion 131 of CPAP apparatus 1A. When controller 130 determines that no stop command to CPAP apparatus 1A has been provided (NO in step S16), the process proceeds to step S3 and returns to obtainment of the temperature of heater 250. When controller 130 determines that the stop command to CPAP apparatus 1A has been provided (YES in step S16), the process proceeds to step S17.

In step S17, controller 130 provides a drive stop command to blower 140. Drive of blower 140 is thus stopped and the blower is turned OFF, and all operations by CPAP apparatus 1A are completed as above.

As controller 130 operates in accordance with the series of control flows described above, a duration for which piezoelectric pump 260 is driven is appropriately controlled so that flexible reservoir 241 is appropriately pressurized and water 500 in an amount necessary for humidification is supplied to heater 250. The humidification operation as shown in FIGS. 9A, 9B, and 9C are thus performed.

As shown in FIG. 9A, the user repeatedly and alternately performs the inhalation operation and the exhalation operation by breathing, and a flow rate of air in first flow path 120 is varied therewith. This variation in flow rate of air is detected by flow rate sensor 133, and controller 130 determines whether the user is performing the inhalation operation or the exhalation operation.

As shown in FIGS. 9B and 9C, when controller 130 determines that the user is performing the inhalation operation, drive of piezoelectric pump 260 is started and drive of piezoelectric pump 260 is stopped at the time point when the cumulative amount of power consumed by heater 250 reaches a prescribed value corresponding to a target amount of humidification. Air to be humidified can thus be humidified in an optimal amount of humidification.

When the configuration is such that the humidification operation described above is completed while the user is performing the inhalation operation, the humidification operation is thus not performed while the user is performing the exhalation operation. Therefore, according to such a configuration, water vapor provided to air in second flow path 220 can be prevented from flowing backward by exhalation by the user to reach first flow path 120. Therefore, failure of various types of equipment (representatively, blower 140) accommodated in first housing 110 due to attachment of moisture thereto or proliferation of germs due to attachment of moisture to an inner wall of first housing 110 can be suppressed, and a CPAP apparatus excellent in aspects of hygiene and ease in maintenance by cleaning can be provided.

As described above, with CPAP apparatus 1A according to the present embodiment, a compact CPAP apparatus capable of efficient humidification can be provided. The reason why the apparatus can be compact is that the humidification mechanism described above (in particular, heater 250 as the vaporizer) can sufficiently be compact, and the reason why humidification can be efficient is that the humidification operation is performed only at timing when humidification is required and hence a total amount of energy necessary for vaporizing water 500 (that is, the sum of an amount of power consumed by heater 250 and an amount of power consumed by piezoelectric pump 260) can be suppressed.

Another reason why humidification can be efficient is ability to significantly suppress energy loss. In a conventional humidification method in which whole water stored in a tank is heated, an amount of heat dissipated from the tank to the outside is unignorably larger than an amount of heat necessary for vaporizing water, and consequently a larger total amount of energy is necessary. In contrast, in the humidification mechanism according to the present embodiment, such waste of energy can be suppressed and consequently humidification can be efficient.

CPAP apparatus 1A according to the present embodiment described above obtains also an effect that, even though the user inadvertently causes the apparatus to topple over, water 500 stored in flexible reservoir 241 can be prevented from entering the inside of blowing unit 100 through second flow path 220 or entering air tube 300. This is because water 500 in a portion located at drain outlet 232 of water supply path 230 communicating with second flow path 220 does not leak to second flow path 220 owing to surface tension of water 500 and thus failure of the equipment described above or flow of water 500 in a liquid state into the airway of the user can be prevented.

From a point of view of such prevention of unintended leakage of water 500 through drain outlet 232, further preferably, a check valve that allows movement of water 500 from water supply path 230 toward heater 250 and restricts movement of water 500 and air that passes through second flow path 220 from heater 250 toward water supply path 230 is provided at drain outlet 232, and instead thereof or in addition thereto, a flow path defining surface of water supply path 230 that defines drain outlet 232 and/or an end surface of drain outlet 232 are/is made water repellent. According to such a construction, not only leakage of water 500 in case of toppling over of CPAP apparatus 1A as described above can be suppressed but also supply of water 500 in an amount more than necessary to heater 250 in the humidification operation can be prevented and the amount of humidification can more reliably and minutely be controlled. In making the vicinity of drain outlet 232 water repellent, the flow path defining surface and/or the end surface of above-described the other end of water supply path 230 provided with drain outlet 232 can be made water repellent. In that case, only a part of the flow path defining surface or only a part of the end surface may be made water repellent.

Furthermore, CPAP apparatus 1A according to the present embodiment described above can obtain also an effect in an aspect of costs, because the humidification mechanism described above is of a very simplified construction and such a component as heater 250 or piezoelectric pump 260 necessary for making up the humidification mechanism is also relatively inexpensive. Therefore, the CPAP apparatus can inexpensively be provided.

Additionally, CPAP apparatus 1A according to the present embodiment described above obtains also a secondary effect that air humidified soon after start of use can be sent into the airway of the user. This is because heater 250 can significantly be reduced in size as described above so that heater 250 can be increased in temperature to a set temperature earlier and consequently the humidification operation can be performed substantially without delay after start of use.

In CPAP apparatus 1A according to the present embodiment described above, from a point of view of the amount of power consumed by heater 250 being in proportion to the amount of humidification, an algorithm for estimating the amount of humidification from the cumulative amount of consumed power is adopted. In actual, however, the amount of power consumed by heater 250 is varied also by such a factor as an ambient temperature, a temperature of water stored in flexible reservoir 241, or an amount of air sent by blower 140. Therefore, for more minute adjustment of the amount of humidification, the amount of humidification is desirably appropriately corrected based on the temperature detected by temperature and humidity sensor 132 or the flow rate detected by flow rate sensor 133.

Second Embodiment

Figure 10:
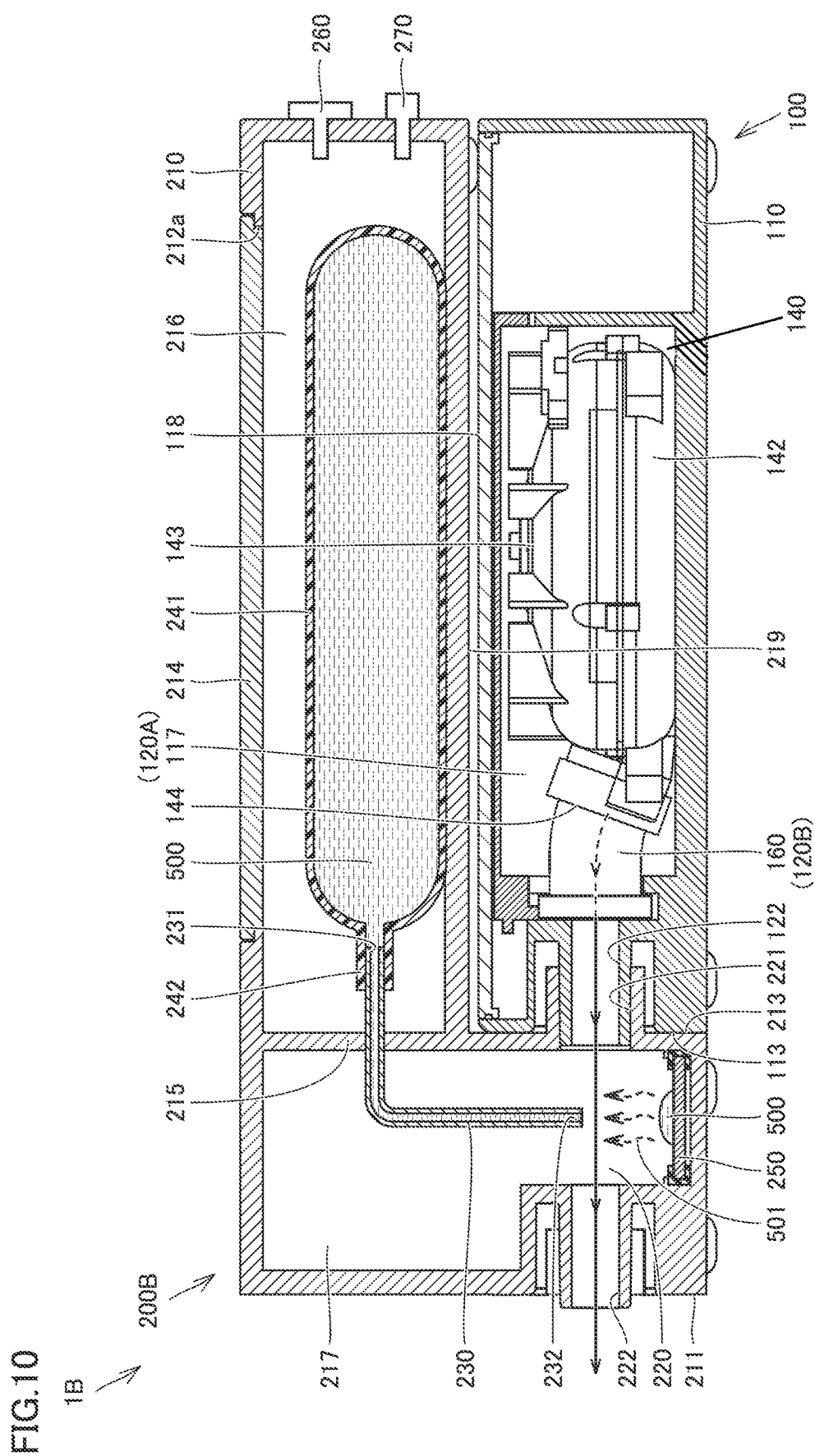
FIG. 10 is a schematic cross-sectional view in the first state of use of a CPAP apparatus according to a second embodiment.

FIG. 10 is a schematic cross-sectional view in the first state of use of a CPAP apparatus according to a second embodiment of the present disclosure. A CPAP apparatus 1B according to the present embodiment will be described below with reference to FIG. 10.

As shown in FIG. 10, CPAP apparatus 1B according to the present embodiment is different from CPAP apparatus 1A according to the first embodiment described above mainly in construction including a differently constructed humidification unit 200B.

Humidification unit 200B does not include a protrusion that protrudes upward from one of the four corners of the upper surface of second housing 210, but instead includes a protrusion that protrudes downward from one of four corners of the lower surface. One of side surfaces of the protrusion provided on the lower surface of second housing 210 defines tube connection surface 211 to which air tube 300 is connected in the first state of use, and another one of the side surfaces of the protrusion described above defines second connection surface 213 connected to blowing unit 100 in the first state of use.

A portion except for the above-described protrusion of the lower surface of second housing 210 defines a placement surface 219 placed on blowing unit 100 in the first state of use. Accordingly, the upper surface of first housing 110 of blowing unit 100 defines a carrier surface 118 on which humidification unit 200B is placed in the first state of use, and the lower surface of first housing 110 defines a placement surface placed on a floor surface or a table in the first state of use.

In CPAP apparatus 1B according to the present embodiment, as humidification unit 200B is placed on blowing unit 100, humidification unit 200B is attached to blowing unit 100. The operation surface where the operation portion of blowing unit 100 is provided is defined by one side surface except for first connection surface 113 of the four side surfaces of first housing 110.

A space inside second housing 210 is divided by partition wall 215 into pressurization chamber 216 and vaporization chamber 217, and vaporization chamber 217 of these chambers is provided to contain as its part, the above-described protrusion provided on the lower surface of second housing 210. Water supply path 230 and heater 250 are arranged in vaporization chamber 217, and heater 250 is provided in a lower portion in the space inside the protrusion described above. Vaporization chamber 217 corresponds to second flow path 220 that connects second inlet 221 and second outlet 222 to each other.

Water supply path 230 is defined by a pipe bent substantially in the L shape, and one end thereof is provided to pass through partition wall 215 to reach pressurization chamber 216. The other end of water supply path 230 is arranged above heater 250 so as to face heater 250. Water supply path 230 thus connects flexible reservoir 241 and heater 250 as the vaporizer to each other.

Above-described one end of water supply path 230 corresponds to connection port 231 detachably connected to flexible reservoir 241 accommodated in pressurization chamber 216 and corresponds to a water feed port through which water 500 stored in flexible reservoir 241 accommodated in pressurization chamber 216 is fed toward water supply path 230. Above-described the other end of water supply path 230 corresponds to drain outlet 232 through which water 500 fed to water supply path 230 through connection port 231 is drained toward heater 250.

Since piezoelectric pump 260 and electromagnetic valve 270 provided to face pressurization chamber 216 are both similar to those in the first embodiment described above, description thereof will not be repeated.

With CPAP apparatus 1B constructed as described above as well, similarly to CPAP apparatus 1A in the first embodiment described above, by appropriately controlling a duration for which piezoelectric pump 260 is driven, flexible reservoir 241 is pressurized so that water 500 in an amount necessary for humidification is supplied to heater 250 and the humidification operation described previously can be performed. Therefore, an effect similar to the effect described in the first embodiment above can be obtained also when the construction is adopted.

FIGS. 11A, 11B, 11C, and 11D are schematic cross-sectional views showing an exemplary construction of the drain outlet of the water supply path shown in FIG. 10. An exemplary construction of water supply path 230 of CPAP apparatus 1B according to the present embodiment will now be described with reference to FIGS. 11A, 11B, 11C, and 11D.

In CPAP apparatus 1B according to the present embodiment, the space inside flexible reservoir 241 is in a hermetically sealed state except for connection port 242. Therefore, unless flexible reservoir 241 is compressed, water 500 basically does not leak from drain outlet 232. From a point of view of more minute adjustment of the amount of humidification, however, preferably, water 500 reliably stays at drain outlet 232 while a pressure is not applied to flexible reservoir 241. Exemplary constructions shown below show some examples for realizing this feature.

Figure 11A:
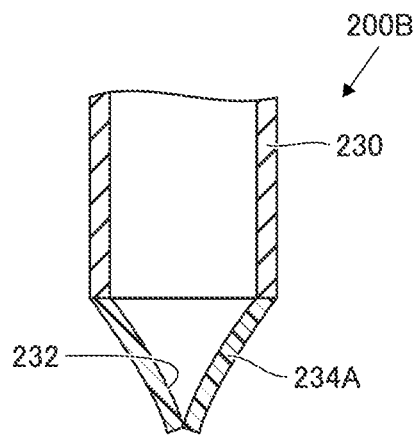
FIGS. 11A, 11B, 11C, and 11D are schematic cross-sectional views showing an exemplary construction of a drain outlet of a water supply path shown in FIG. 10.

In an exemplary construction shown in FIG. 11A, a check valve 234A is provided at above-described the other end of water supply path 230. Check valve 234A is formed, for example, from an elastic body, and drain outlet 232 of water supply path 230 is thus defined by check valve 234A. In this case, check valve 234A normally does not allow movement of water 500 from water supply path 230 toward heater 250. On the other hand, during a period from opening of check valve 234A by increase in internal pressure in flexible reservoir 241 due to compression of flexible reservoir 241 until stop of increase in internal pressure, movement of water 500 from water supply path 230 toward heater 250 is allowed.

Figure 11B:
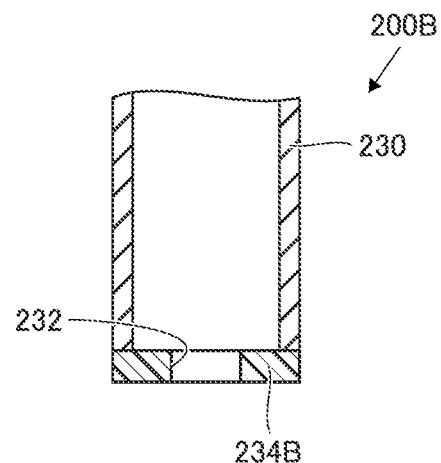
Figure 11C:
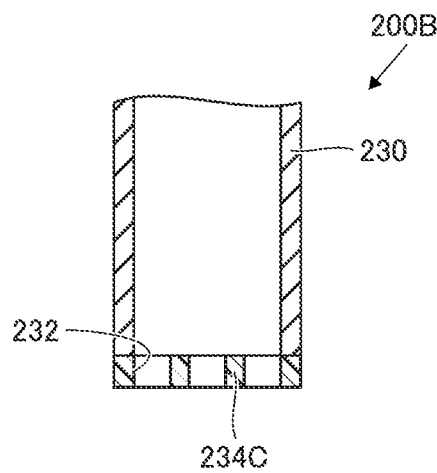
Figure 11D:
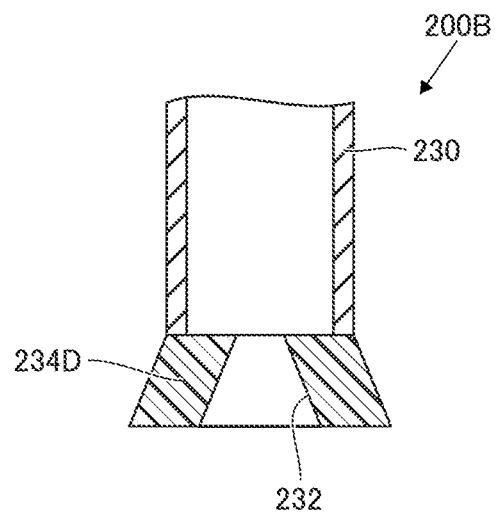

In exemplary constructions shown in FIGS. 11B, 11C, and 11D, above-described the other end of water supply path 230 is provided with nozzles 234B to 234D. Nozzles 234B to 234D each include drain outlet 232 smaller than an inner diameter of water supply path 230, so that surface tension produced in a part of water 500 in contact with drain outlet 232 is increased. According to such a construction, movement of water 500 from water supply path 230 toward heater 250 is normally not allowed, and water 500 is pushed out of water supply path 230 toward heater 250 owing to increase in internal pressure in flexible reservoir 241 as a result of compression of flexible reservoir 241.

Nozzle 234B in a shape shown in FIG. 11B is constructed such that a single hole defines drain outlet 232, and nozzle 234C in a shape shown in FIG. 11C is constructed such that a plurality of holes define drain outlet 232. Nozzle 234D in a shape shown in FIG. 11D is constructed such that a single hole increasing in cross-sectional area downward defines drain outlet 232. With nozzle 234C in the shape shown in FIG. 11C, water 500 is supplied to heater 250 like a shower, and with nozzle 234D in the shape shown in FIG. 11D, water 500 is supplied over a wider range of heater 250, so that an effect of vaporization of water 500 in heater 250 more accelerated than with nozzle 234B in the shape shown in FIG. 11B is obtained.

Check valve 234A shown in FIG. 11A described above and nozzles 234B to 234D shown in FIGS. 11B, 11C, and 11D described above may each be formed from a water repellent member. In that case, since drain outlet 232 defined by each of check valve 234A and nozzles 234B to 234D repels water 500, movement of water 500 from water supply path 230 toward heater 250 is normally not allowed and water 500 can be pushed out of water supply path 230 toward heater 250 owing to increase in internal pressure in flexible reservoir 241 as a result of compression of flexible reservoir 241.

Third Embodiment

Figure 12:
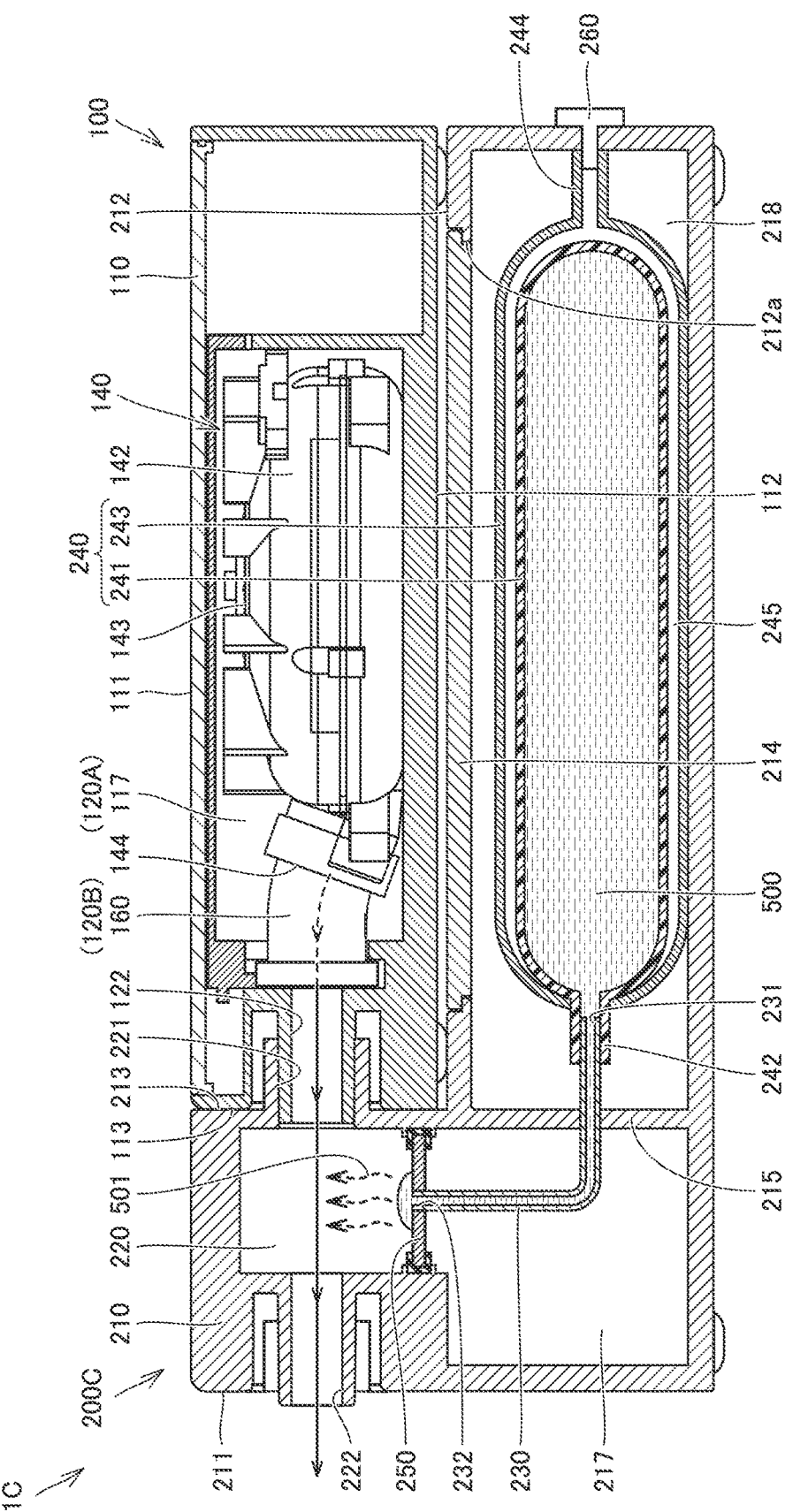
FIG. 12 is a schematic cross-sectional view in the first state of use of a CPAP apparatus according to a third embodiment.

FIG. 12 is a schematic cross-sectional view in the first state of use of a CPAP apparatus according to a third embodiment of the present disclosure. A CPAP apparatus 1C according to the present embodiment will be described below with reference to FIG. 12.

As shown in FIG. 12, CPAP apparatus 1C according to the present embodiment is different from CPAP apparatus 1A according to the first embodiment described above mainly in construction including a differently constructed humidification unit 200C.

Though second housing 210 of humidification unit 200C is basically similar in construction to second housing 210 of humidification unit 200A according to the first embodiment, in the space therein, a space where flexible reservoir 241 is accommodated is not provided as the pressurization chamber but provided simply as an accommodation chamber 218. In other words, accommodation chamber 218 does not necessarily have to hermetically be sealed, and accordingly, a sealing material such as gasket does not have to be provided either between a portion defining opening 212a provided in stage surface 212 of second housing 210 and lid 214. Piezoelectric pump 260 should only be provided in the wall of second housing 210 and the electromagnetic valve does not have to be provided.

Flexible reservoir 241 accommodated in accommodation chamber 218 described above is provided as a part of a two-ply bag 240 covered with a bag-shaped member 243 where flexible reservoir 241 is accommodated. Preferably, bag-shaped member 243 is formed from a hard member less likely to deform than flexible reservoir 241 and corresponds to the accommodation portion where flexible reservoir 241 is accommodated. Bag-shaped member 243 is formed, for example, from a resin member or a metal member like a film.

Flexible reservoir 241 and bag-shaped member 243 that make up two-ply bag 240 are integrated by being joined to each other by bonding or welding. Connection port 242 of flexible reservoir 241 is drawn outward through bag-shaped member 243, and a connection port 244 different from connection port 242 of flexible reservoir 241 described above is provided at a prescribed position in bag-shaped member 243.

A space inside flexible reservoir 241 (that is, a space filled with water 500) thus communicates with an external space through connection port 242, and a pressurization space 245 which is a space outside flexible reservoir 241 and inside bag-shaped member 243 communicates with the external space through connection port 244.

While two-ply bag 240 is accommodated in accommodation chamber 218, connection port 242 of flexible reservoir 241 is connected to connection port 231 of water supply path 230 and connection port 244 of bag-shaped member 243 is connected to piezoelectric pump 260. Water can thus be fed from flexible reservoir 241 to water supply path 230 and pressurization space 245 can be pressurized by piezoelectric pump 260.

As described above, in the present embodiment, bag-shaped member 243 is formed from a member harder than flexible reservoir 241. Therefore, when pressurization space 245 is pressurized by driving piezoelectric pump 260, the pressure is mainly applied to flexible reservoir 241 and flexible reservoir 241 is thus more efficiently compressed.

With this compressive force, water 500 stored in flexible reservoir 241 is introduced into water supply path 230 through connection ports 231 and 242, and thereafter pushed out of water supply path 230 through drain outlet 232 and supplied to heater 250. Water supplied to heater 250 is immediately heated and vaporized by heater 250 to become water vapor 501, and water vapor is provided to air that passes through second flow path 220.

With CPAP apparatus 1C constructed as described above as well, as in CPAP apparatus 1A in the first embodiment described above, by appropriately controlling a duration for which piezoelectric pump 260 is driven, flexible reservoir 241 is pressurized so that water 500 in an amount necessary for humidification is supplied to heater 250 and the humidification operation described previously can be performed. Therefore, an effect similar to the effect described in the first embodiment above can be obtained also when the construction is adopted.

Though an example in which accommodation chamber 218 for accommodating two-ply bag 240 is provided in second housing 210 is illustrated in the present embodiment, accommodation chamber 218 does not have to be provided and two-ply bag 240 may externally be attached to second housing 210. In such a construction, humidification unit 200C as a whole including two-ply bag 240 can significantly be reduced in size, and furthermore, while the apparatus is not used, two-ply bag 240 not filled with water 500 is also foldable and portable. Therefore, a highly convenient CPAP apparatus can be provided.

Fourth Embodiment

Figure 13:
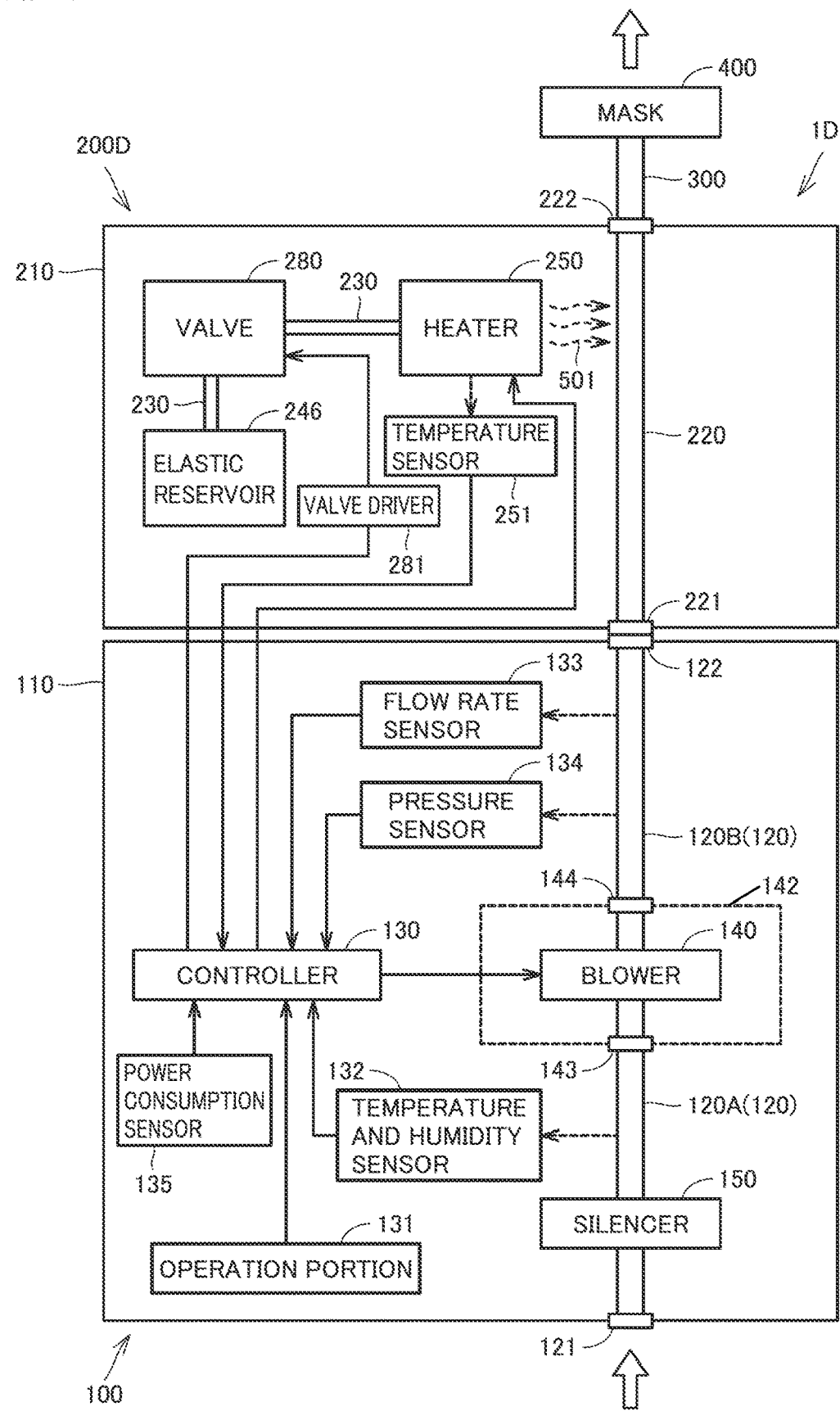
FIG. 13 is a diagram showing a configuration of a functional block in the first state of use of a CPAP apparatus according to a fourth embodiment.
Figure 14:
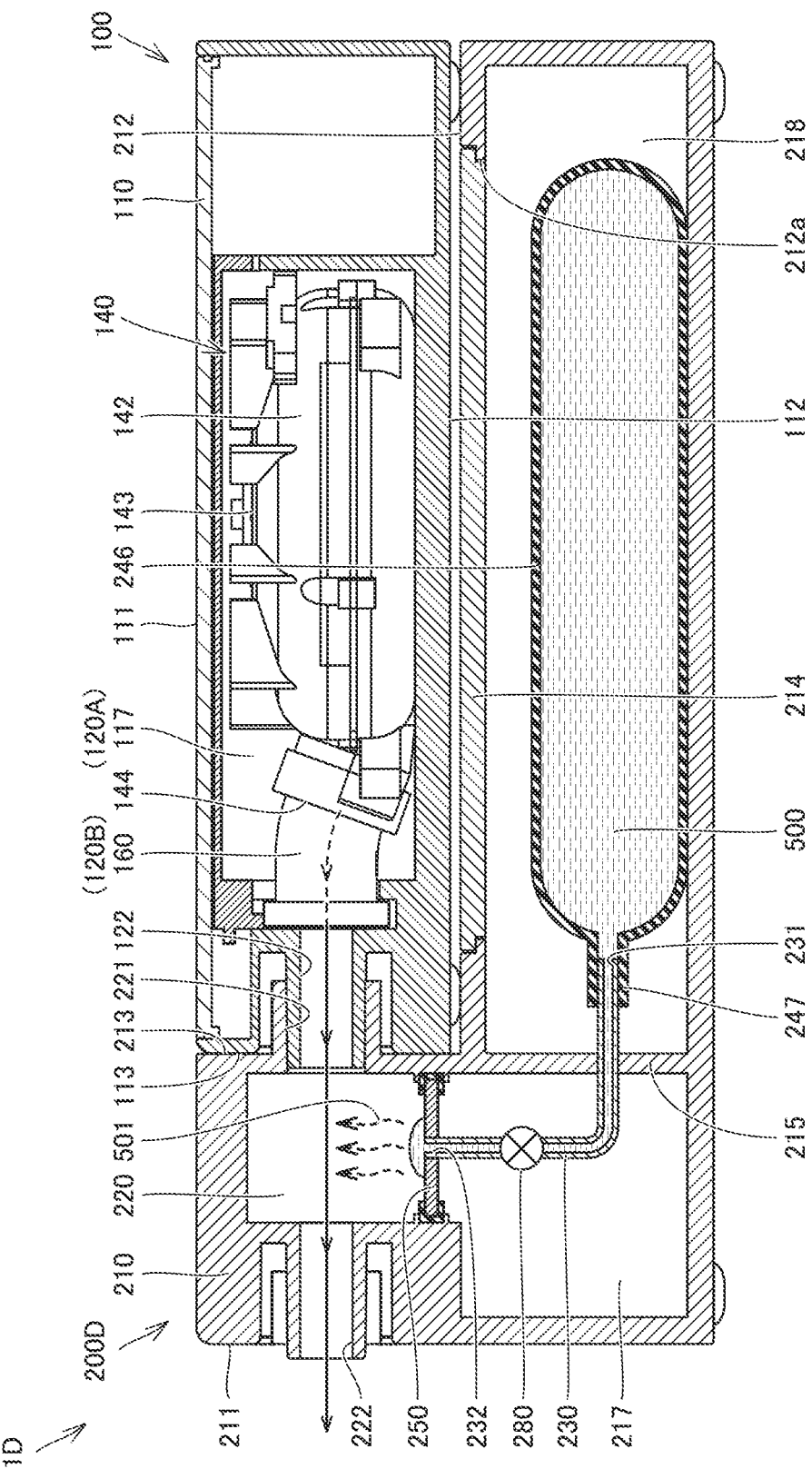
FIG. 14 is a schematic cross-sectional view in the first state of use of the CPAP apparatus according to the fourth embodiment.

FIG. 13 is a diagram showing a configuration of a functional block in the first state of use of a CPAP apparatus according to a fourth embodiment of the present disclosure and FIG. 14 is a schematic cross-sectional view in the first state of use of the CPAP apparatus. The configuration of the functional block in the first state of use and a detailed structure of a CPAP apparatus 1D according to the present embodiment will initially be described with reference to FIGS. 13 and 14.

As shown in FIGS. 13 and 14, CPAP apparatus 1C according to the present embodiment is different from CPAP apparatus 1A according to the first embodiment described above mainly in construction including a differently constructed humidification unit 200D. Humidification unit 200A according to the first embodiment described above is constructed such that water 500 is supplied to heater 250 as the vaporizer by externally pressurizing flexible reservoir 241, whereas humidification unit 200D according to the present embodiment instead allows supply of water 500 to heater 250 by making use of elastic resilience of an elastic reservoir 246 itself.

Though second housing 210 of humidification unit 200D of CPAP apparatus 1D is basically similar in construction to second housing 210 of humidification unit 200A according to the first embodiment, in the space therein, a space where elastic reservoir 246 is accommodated is not provided as the pressurization chamber but provided simply as accommodation chamber 218. In other words, accommodation chamber 218 does not necessarily have to hermetically be sealed, and accordingly, a sealing material such as gasket does not have to be provided either between a portion defining opening 212a provided in stage surface 212 of second housing 210 and lid 214. The piezoelectric pump and the electromagnetic valve are not provided in the wall of second housing 210.

A valve 280 is provided in a part of water supply path 230 located in vaporization chamber 217 of second housing 210. While valve 280 is open, it allows flow of water 500 through water supply path 230, and while valve 280 is closed, it cuts off flow of water 500 through water supply path 230. Valve 280 can be driven, for example, by a valve driver 281 implemented by a motor, and valve driver 281 switches valve 280 to any of an open state and a closed state.

Elastic reservoir 246 accommodated in accommodation chamber 218 described above is formed from a bag-shaped member where water 500 is stored, and includes a connection port 247 through which stored water 500 can be drained. Elastic reservoir 246 is formed from a member elastically freely deformable without allowing leakage of water 500 stored therein, and accommodated in accommodation chamber 218 described above such that it can be put into and taken out of accommodation chamber 218. Connection port 247 provided in elastic reservoir 246 can detachably be connected to connection port 231 of water supply path 230. Elastic reservoir 246 is formed, for example, from a member made of rubber.

Elastic reservoir 246 is elastically inflated and deformed by injection of water 500 thereinto. In other words, while external force is not applied, a space inside elastic reservoir 246 is sufficiently small or there is no space provided therein, and elastic reservoir 246 is like a balloon so to speak.

Water supply path 230, elastic reservoir 246, heater 250, valve 280, and valve driver 281 described above mainly correspond to the humidification mechanism that humidifies gas to be humidified sent by blower 140. The humidification operation by the humidification mechanism is performed by setting valve 280 to the open state (that is, opening the valve) for a prescribed time period.

More specifically, by adopting the construction described above, when valve 280 is in the open state, water 500 stored in elastic reservoir 246 is introduced into water supply path 230 through connection ports 247 and 231 owing to elastic resilience of elastic reservoir 246, thereafter pushed out of water supply path 230 through drain outlet 232, and supplied to heater 250. Water supplied to heater 250 is immediately heated and vaporized by heater 250 to become water vapor 501, and water vapor is provided to air that passes through second flow path 220.

When valve 280 is closed, supply of water 500 to heater 250 is stopped by cut-off of flow of water 500 through water supply path 230 and the humidification operation is accordingly also stopped.

Figure 15:
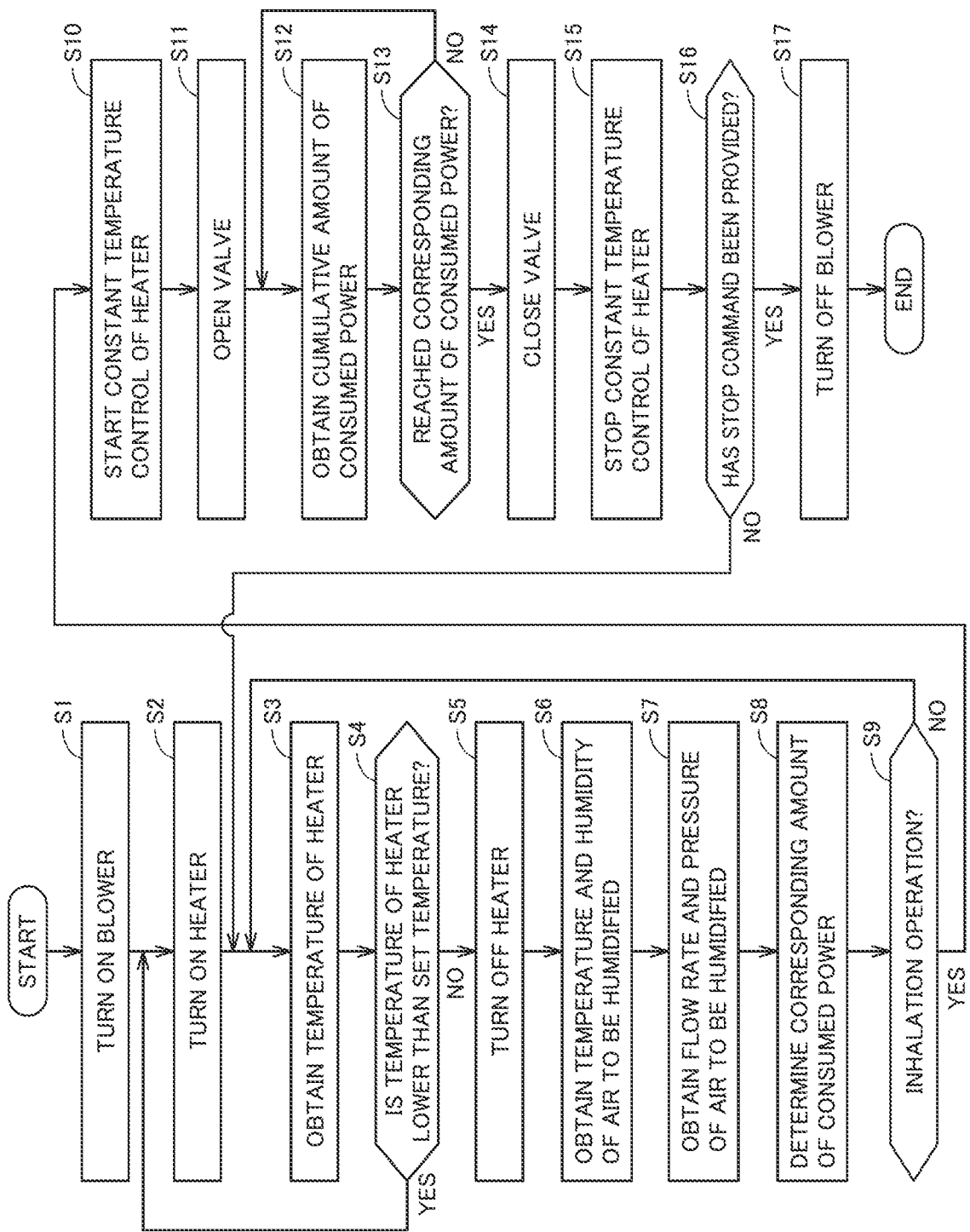
FIG. 15 is a flowchart showing an operation of the controller in the first state of use of the CPAP apparatus according to the fourth embodiment.
Figure 16:
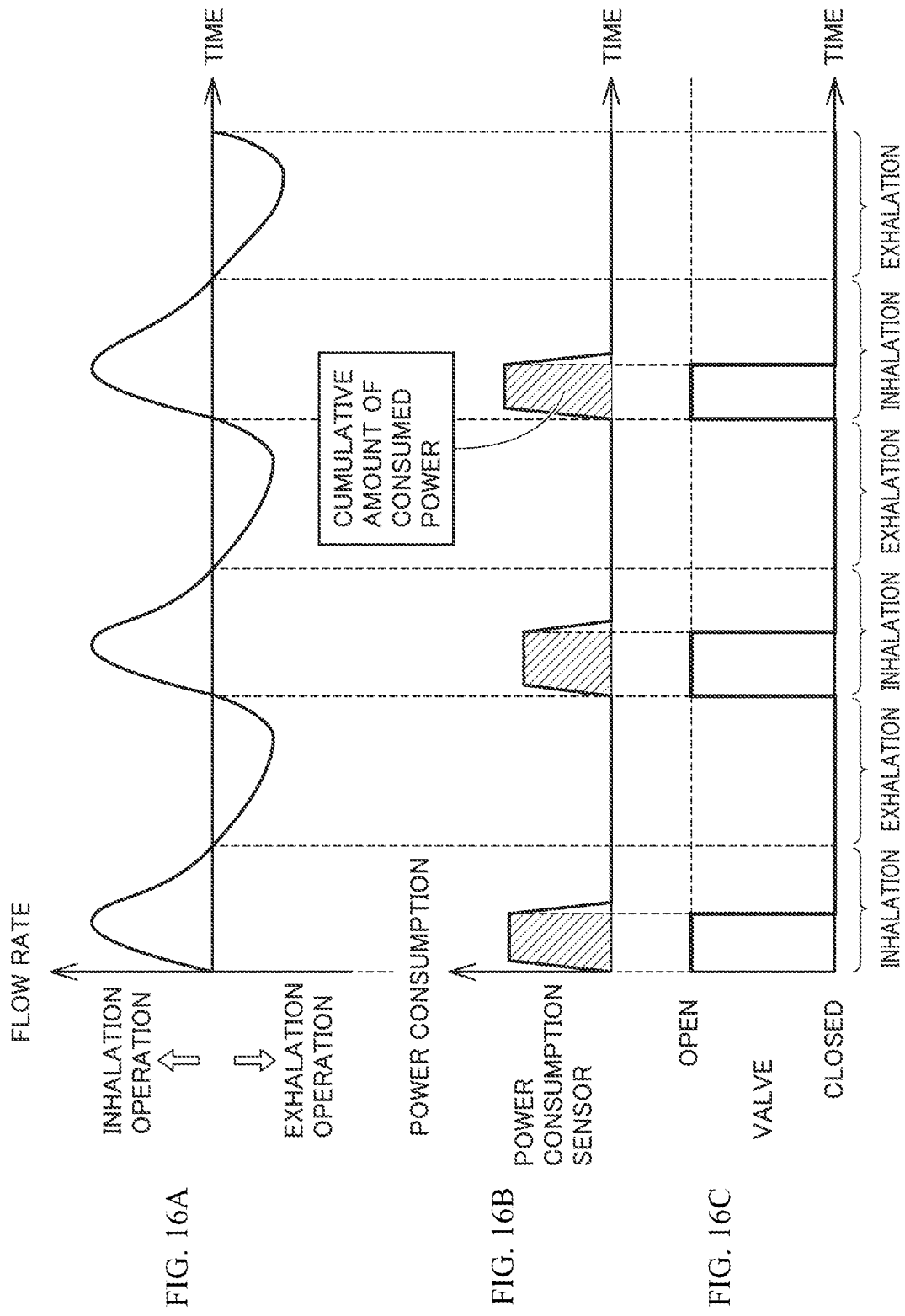
FIGS. 16A, 16B, and 16C are timing charts for illustrating a humidification operation by the CPAP apparatus according to the fourth embodiment.

FIG. 15 is a flowchart showing an operation of the controller in the first state of use of the CPAP apparatus according to the present embodiment. FIGS. 16A, 16B, and 16C are timing charts for illustrating the humidification operation by the CPAP apparatus according to the present embodiment. Details of the humidification operation by CPAP apparatus 1D according to the present embodiment will now be described with reference to FIGS. 15 and 16A, 16B, and 16C.

As shown in FIG. 15, a control flow of controller 130 in CPAP apparatus 1D according to the present embodiment is in conformity with the control flow shown in FIG. 8, and the difference resides only in that valve 280 is opened in step S11 and valve 280 is closed in step S14. Valve 280 is opened and closed by controller 130 providing an operation command to valve driver 281.

As controller 130 operates in accordance with a series of control flows shown in FIG. 15, a duration for which valve 280 is open is appropriately controlled so that water 500 in an amount necessary for humidification is supplied to heater 250. The humidification operation as shown in FIGS. 16A, 16B, and 16C are thus performed.

Therefore, CPAP apparatus 1D constructed as described above can also obtain an effect similar to the effect described in the first embodiment above and a compact CPAP apparatus capable of efficient humidification can be provided.

Though an example in which accommodation chamber 218 where elastic reservoir 246 is accommodated is provided in second housing 210 is illustrated in the present embodiment, accommodation chamber 218 does not have to be provided and elastic reservoir 246 may externally be attached to second housing 210. According to such a construction, humidification unit 200D as a whole including elastic reservoir 246 can significantly be reduced in size, and furthermore, while the apparatus is not used, elastic reservoir 246 not filled with water 500 is also foldable and portable. Therefore, a highly convenient CPAP apparatus can be provided.

Fifth Embodiment

Figure 17:
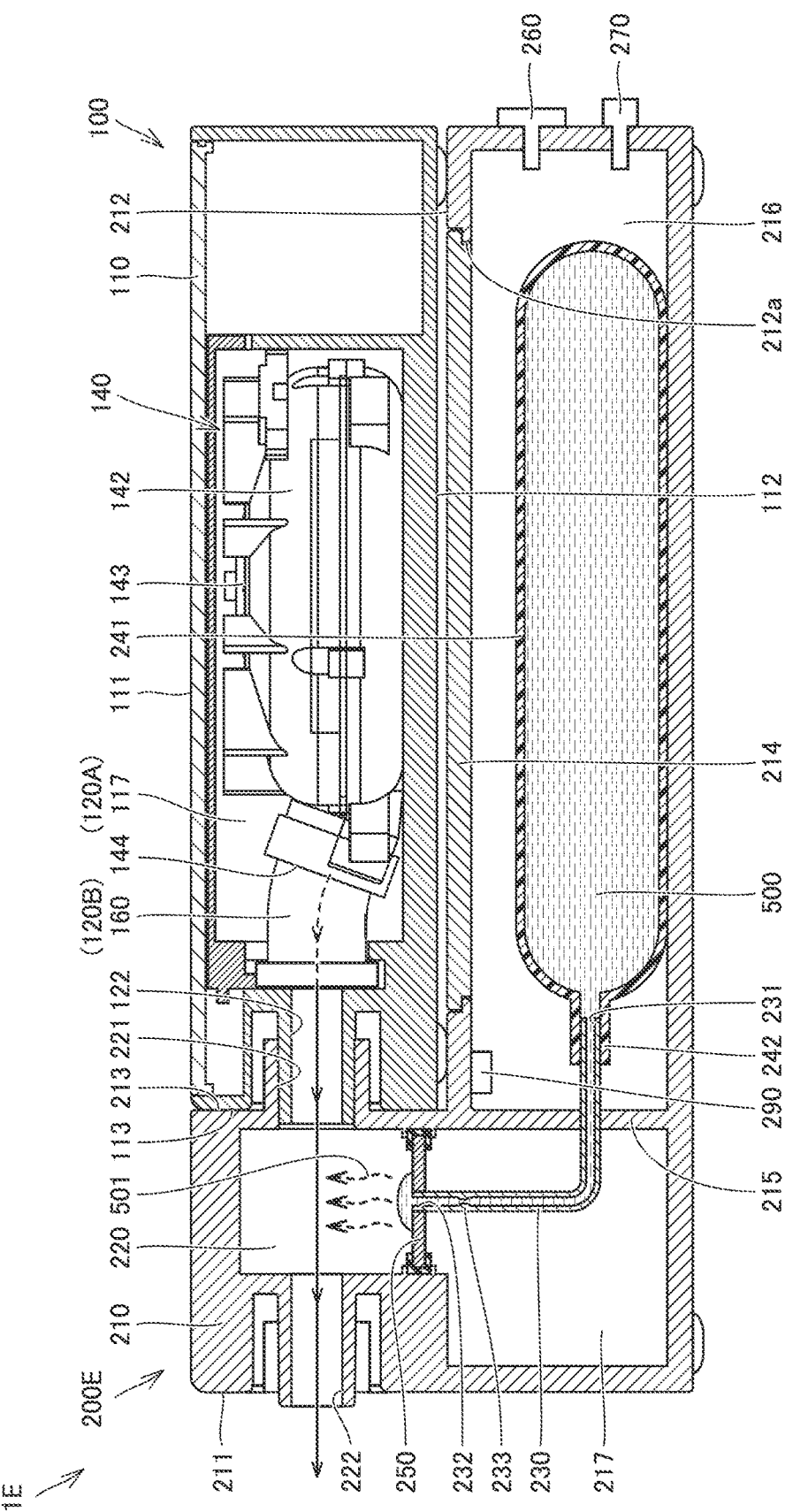
FIG. 17 is a schematic cross-sectional view in the first state of use of a CPAP apparatus according to a fifth embodiment.
Figure 18:
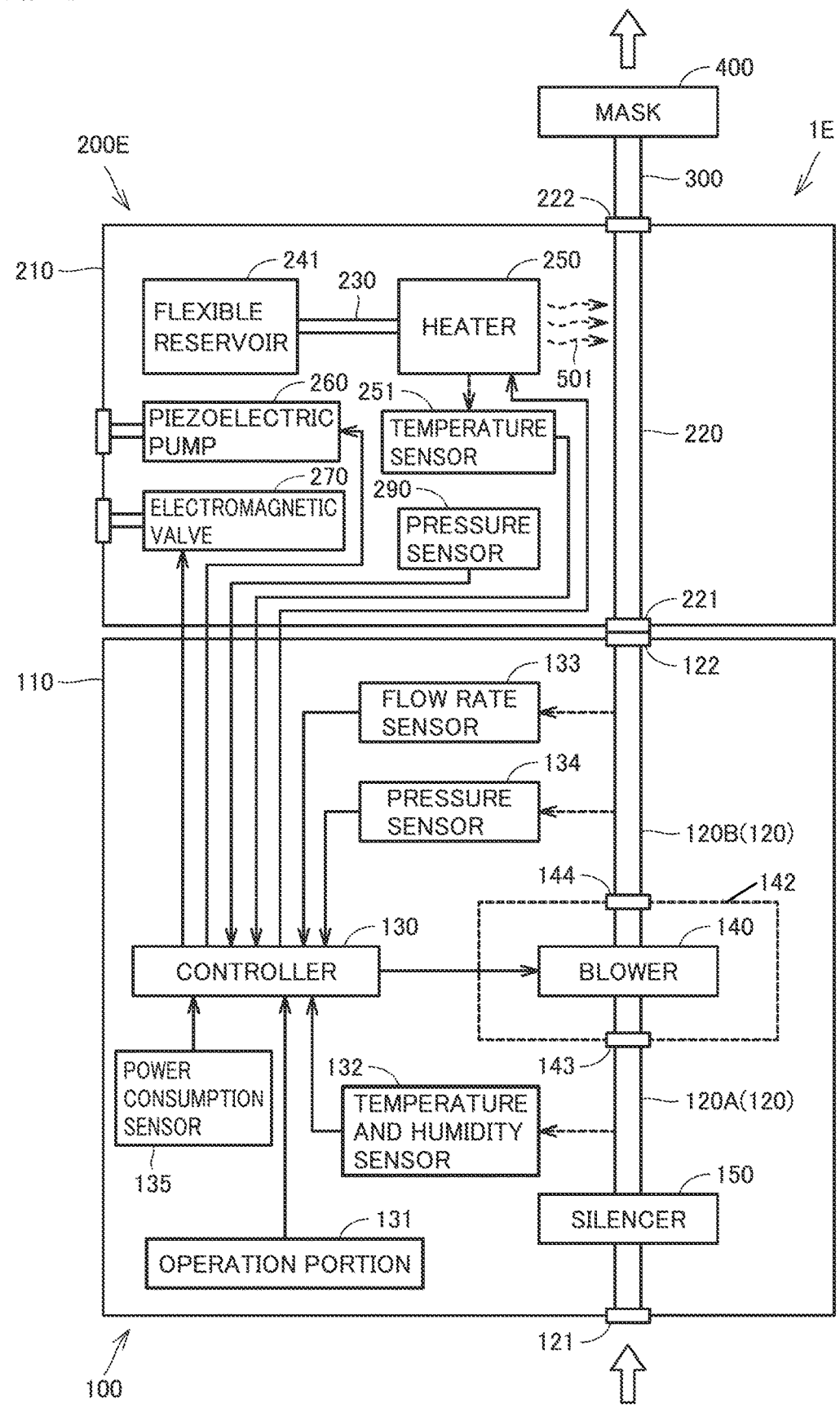
FIG. 18 is a diagram showing a configuration of a functional block in the first state of use of the CPAP apparatus according to the fifth embodiment.

FIG. 17 is a schematic cross-sectional view in the first state of use of a CPAP apparatus according to a fifth embodiment of the present disclosure and FIG. 18 is a diagram showing a configuration of a functional block in the first state of use of the CPAP apparatus. A CPAP apparatus 1E according to the present embodiment will be described below with reference to FIGS. 17 and 18.

As shown in FIGS. 17 and 18, CPAP apparatus 1E according to the present embodiment is different from CPAP apparatus 1A according to the first embodiment described above mainly in construction including a differently constructed humidification unit 200E.

Specifically, pressurization chamber 216 as the accommodation portion provided in second housing 210 of humidification unit 200E is provided with a pressure sensor 290 as the pressure sensing portion. More specifically, pressure sensor 290 is arranged in a space outside flexible reservoir 241 and inside pressurization chamber 216 so as to sense a pressure in pressurization chamber 216. The pressure sensed by pressure sensor 290 is provided to controller 130 and mainly used for the humidification operation by the humidification mechanism.

In CPAP apparatus 1E according to the present embodiment, unlike CPAP apparatus 1A according to the first embodiment described above, an amount of humidification by the humidification mechanism is adjusted by control by controller 130, of drive of piezoelectric pump 260 (for example, control of a duration of drive) based on the pressure in pressurization chamber 216 sensed by pressure sensor 290 described above.

In CPAP apparatus 1E according to the present embodiment, flexible reservoir 241 accommodated in pressurization chamber 216 is compressed by driving piezoelectric pump 260, so that some of water 500 stored in flexible reservoir 241 is supplied to heater 250 through water supply path 230. Therefore, the pressure in pressurization chamber 216 establishes prescribed correlation with an amount of water 500 (that is, an amount of humidification) pushed out of flexible reservoir 241.

Therefore, under feedback control by controller 130, while the pressure in pressurization chamber 216 is sensed, piezoelectric pump 260 is appropriately driven based on the sensed pressure, so that flexible reservoir 241 is appropriately pressurized and consequently the amount of humidification by the humidification mechanism can be adjusted.

In humidification unit 200E, an orifice 233 smaller in flow path cross-sectional area than another portion of water supply path 230 having connection port 231 as one end connected to flexible reservoir 241 and having drain outlet 232 as the other end connected to heater 250 is provided at a position in the middle of water supply path 230. Orifice 233 is provided at a position in the middle of water supply path 230 for forming a portion higher in flow path resistance than other portions.

By thus providing orifice 233 at the position in the middle of water supply path 230, an amount of water 500 supplied to heater 250 through water supply path 230 can further be smaller. As orifice 233 functions as a high flow path resistance portion, a ratio of an amount of supply of water 500 to heater 250 against increase in pressure in pressurization chamber 216 can be lowered, and consequently water 500 can be supplied to heater 250 at a low flow rate in a stable manner.

Therefore, according to such a construction, variation in amount of supply of water 500 due to variation in pressure can be suppressed and an amount of humidification by the humidification mechanism can highly accurately be adjusted. Orifice 233 does not necessarily have to be provided at the position in the middle of water supply path 230 but may be provided at an end on a side of connection port 231 or on a side of drain outlet 232 of water supply path 230.

CPAP apparatus 1E constructed as described above can also obtain an effect similar to the effect described in the first embodiment above and a compact CPAP apparatus capable of efficient humidification can be provided.

(Other Forms)

Though an example in which the present disclosure is applied to the CPAP apparatus as the humidification and blowing apparatus for respiratory organs is described by way of example in the first to fifth embodiments above, the present disclosure is applicable also to a steam inhaler or an oxygen inhaler other than the CPAP apparatus. The present disclosure is applicable to any apparatus so long as the apparatus includes the humidification apparatus and naturally applicable also to an apparatus other than the humidification and blowing apparatus for respiratory organs. Furthermore, the present disclosure is effectively applicable also to the humidification apparatus used alone.

Though an example in which the heater as the vaporizer that heats water is employed is described by way of example in the first to fifth embodiments above, the vaporizer does not necessarily have to be constructed as such, and any component capable of vaporizing water can be employed as the vaporizer. When an atomizer (for example, an ultrasonic vibrator) is provided instead of the vaporizer, the apparatus can be made use of as an atomization apparatus. Examples of the atomization apparatus include a nebulizer as an atomization apparatus for respiratory organs.

Though an example in which the piezoelectric pump as the ambient air introduction source is employed as the pressurization source is described by way of example in the first to third and fifth embodiments above, the pressurization source that pressurizes the pressurization chamber does not necessarily have to include the ambient air introduction source that introduces ambient air into the pressurization chamber. When the pressurization source includes the ambient air introduction source as well, the ambient air introduction source does not necessarily have to include the piezoelectric pump, and any component capable of delivering ambient air can be employed as the ambient air introduction source.

Though an example in which a component formed from a low-profile sack-shaped member is provided as the flexible reservoir and the elastic reservoir is described by way of example in the first to fifth embodiments above, the shape of the flexible reservoir and the elastic reservoir is not particularly restricted, and the reservoir may be formed from a sack-shaped member which is not of a low profile (for example, like a ball or a rod) or a sack-shaped member in a special shape such as bellows.

Characteristic features disclosed in the first to fifth embodiments described above can be combined with one another unless they depart from the gist of the present disclosure.

The embodiments disclosed herein are thus illustrative and non-restrictive in every respect. The technical scope of the present disclosure is defined by the terms of the claims and is intended to include any modifications within the scope and meaning equivalent to the terms of the claims.

REFERENCE SIGNS LIST 1A to 1E CPAP apparatus; 100 blowing unit; 110 first housing; 111 operation surface; 112 placement surface; 113 first connection surface; 114 bulkhead; 115 wide portion; 116 narrow portion; 117 blower chamber; 118 carrier surface; 120 first flow path; 120A upstream flow path portion; 120B downstream flow path portion; 121 first inlet; 122 first outlet; 130 controller; 131 operation portion; 132 temperature and humidity sensor; 133 flow rate sensor; 134 pressure sensor; 135 power consumption sensor; 140 blower; 141 impeller; 142 casing; 143 suction port; 144 emission port; 150 silencer; 160 hose; 170 filter; 171 filter cover; 200A to 200E humidification unit; 210 second housing; 211 tube connection surface; 212 stage surface; 212a opening; 213 second connection surface; 214 lid; 215 partition wall; 216 pressurization chamber; 217 vaporization chamber; 218 accommodation chamber; 219 placement surface; 220 second flow path; 221 second inlet; 222 second outlet; 230 water supply path; 231 connection port; 232 drain outlet; 233 orifice; 234A check valve; 234B to 234D nozzle; 240 two-ply bag; 241 flexible reservoir; 242 connection port; 243 bag-shaped member; 244 connection port; 245 pressurization space; 246 elastic reservoir; 247 connection port; 250 heater; 251 temperature sensor; 260 piezoelectric pump; 270 electromagnetic valve; 280 valve; 281 valve driver; 290 pressure sensor; 300 air tube; 400 mask; 500 water; 501 water vapor

The invention claimed is:

1. A humidification apparatus comprising:
a bag-shaped flexible reservoir adapted to store water;
a vaporizer configured to vaporize water supplied from the flexible reservoir;
a water supply path having a first end detachably connected to the flexible reservoir and a second end connected to the vaporizer;
a chamber that houses the flexible reservoir;
a pressurization source configured to compress the flexible reservoir by pressurizing a space outside the flexible reservoir and inside the chamber;
a electromagnetic valve configured to emit air from the chamber to outside the chamber; and
a controller configured to control an operation of the pressurization source,
wherein compression of the flexible reservoir by the pressurization source causes water stored in the flexible reservoir to be supplied to the vaporizer through the water supply path.

2. The humidification apparatus according to claim 1, wherein the pressurization source is configured to introduce ambient air into the space outside the flexible reservoir and inside the chamber.

3. The humidification apparatus according to claim 2, wherein the pressurization source comprises a piezoelectric pump.

4. The humidification apparatus according to claim 1, wherein the chamber is defined at least in part by a pressure bulkhead.

5. The humidification apparatus according to claim 1, wherein:
the chamber is bag-shaped, and
the flexible reservoir and the bag-shaped chamber are joined and integrated with each other to be in a two-ply bag structure.

6. The humidification apparatus according to claim 1, further comprising:
a check valve configured to allow a flow of water from the water supply path toward the vaporizer, and to restrict the flow of water from the vaporizer toward the water supply path,
wherein the check valve is at the second end of the water supply path.

7. The humidification apparatus according to claim 1, wherein a surface of the water supply path is water repellent.

8. The humidification apparatus according to claim 1, wherein the water supply path comprises an orifice.

9. The humidification apparatus according to claim 1, wherein the vaporizer comprises a heater configured to heat the supplied water.

10. The humidification apparatus according to claim 9, further comprising:
a temperature sensor configured to detect a temperature of the heater; and
a power consumption sensor configured to detect power consumed by the heater, wherein:
the controller is further configured to control an output from the heater to maintain a constant temperature of the heater based on the temperature detected by the temperature sensor, and
the controller is further configured to control an amount of water supplied to the vaporizer based on an amount of power consumption detected by the power consumption sensor, thereby adjusting an amount of humidification.

11. A humidification and blowing apparatus for respiratory organs comprising:
a blowing apparatus comprising a blower configured to supply gas into an airway of a user; and
the humidification apparatus according to claim 1,
wherein an air current generated as the blower is driven is humidified by the humidification apparatus.

12. The humidification and blowing apparatus for respiratory organs according to claim 11, further comprising:
a breathing state sensor configured to sense a breathing state of the user, wherein:
the controller is further configured to determine whether the user is inhaling or exhaling based on the breathing state sensor,
when the controller determines that the user is inhaling, the humidification apparatus is configured to perform a humidification operation, and
when the controller determines that the user is exhaling, the humidification apparatus is configured to stop the humidification operation.

13. The humidification apparatus according to claim 1, further comprising:
a pressure sensor configured to sense a pressure in the space outside the flexible reservoir and inside the chamber, wherein the controller is further configured to control an amount of supply of water to the vaporizer based on the pressure sensed by the pressure sensor, thereby adjusting an amount of humidification.

14. A humidification and blowing apparatus for respiratory organs comprising:
a humidification apparatus contained within a humidification housing, the humidification apparatus comprising:
a bag-shaped elastic reservoir adapted to store water;
a vaporizer configured to vaporize water supplied from the flexible reservoir;
a water supply path having a first end detachably connected to the flexible reservoir and a second end connected to the vaporizer;
a valve in the water supply path, wherein the valve is configured to allow a flow of water through the water supply path when the valve is in an open state, and is configured to restrict the flow of water through the water supply path when the valve is in a closed state;
a valve driver configured to selectively switch the valve between the open state and the closed state; and
a controller configured to control an operation of the valve driver, wherein:
the elastic reservoir is elastically inflated and deformed by injection of water into an inside of the elastic reservoir, and
water stored in the elastic reservoir is supplied to the vaporizer through the water supply path when the valve is in the open state due to an elastic resilience of the elastic reservoir; and
a blowing apparatus comprising a blower configured to supply gas into an airway of a user,
wherein the blowing apparatus is fully contained within a detachable chamber located above the elastic reservoir in an assembled position,
wherein the blower is fully contained within the detachable chamber in a detached position
wherein the detachable chamber includes a first outlet and the humidification housing includes a second outlet, and
wherein the first outlet and the second outlet are axially aligned.

15. The humidification and blowing apparatus for respiratory organs according to claim 14, wherein a surface of the water supply path is water repellent.

16. The humidification and blowing apparatus for respiratory organs according to claim 14, wherein the water supply path comprises an orifice.

17. The humidification and blowing apparatus for respiratory organs according to claim 14, wherein the vaporizer comprises a heater configured to heat the supplied water.

18. The humidification and blowing apparatus for respiratory organs according to claim 17, further comprising:

a temperature sensor configured to detect a temperature of the heater; and
a power consumption sensor configured to detect power consumed by the heater, wherein:
the controller is further configured to control an output from the heater to maintain a constant temperature of the heater based on the temperature detected by the temperature sensor, and
the controller is further configured to control an amount of water supplied to the vaporizer based on an amount of power consumption detected by the power consumption sensor, thereby adjusting an amount of humidification.

19. A humidification and blowing apparatus for respiratory organs according to claim 14, wherein an air current generated as the blower is driven is humidified by the humidification apparatus.

20. The humidification and blowing apparatus for respiratory organs according to claim 19, further comprising:
a breathing state sensor configured to sense a breathing state of the user, wherein:
the controller is further configured to determine whether the user is inhaling or exhaling based on the breathing state sensor,
when the controller determines that the user is inhaling, the humidification apparatus is configured to perform a humidification operation, and
when the controller determines that the user is exhaling, the humidification apparatus is configured to stop the humidification operation.

21. A humidification apparatus comprising:
a bag-shaped flexible reservoir adapted to store water;
a vaporizer configured to vaporize water supplied from the flexible reservoir;
a water supply path having a first end detachably connected to the flexible reservoir and a second end connected to the vaporizer;
a chamber that houses the flexible reservoir;
a pressurization source configured to compress the flexible reservoir by pressurizing a space outside the flexible reservoir and inside the chamber;
an exhaust valve that is provided separately from the pressurization source, wherein the exhaust valve is configured to provide a pressure reduction in the chamber prior to a removal of the flexible reservoir, and wherein the exhaust valve is an electromagnetic valve; and
a controller configured to control an operation of the pressurization source,
wherein compression of the flexible reservoir by the pressurization source causes water stored in the flexible reservoir to be supplied to the vaporizer through the water supply path.

* * * * *